United States Patent
Lai et al.

(10) Patent No.: US 11,905,322 B2
(45) Date of Patent: Feb. 20, 2024

(54) ENGINEERED PD-1 VARIANTS

(71) Applicant: Albert Einstein College of Medicine, Bronx, NY (US)

(72) Inventors: Jonathan R. Lai, Dobbs Ferry, NY (US); Steven Almo, Pelham, NY (US); Nina Liu, Larchmont, NY (US); Julia Frei, Bronx, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 136 days.

(21) Appl. No.: 17/306,435

(22) Filed: May 3, 2021

(65) Prior Publication Data

US 2022/0098274 A1    Mar. 31, 2022

Related U.S. Application Data

(63) Continuation of application No. 16/096,369, filed as application No. PCT/US2017/031681 on May 9, 2017, now Pat. No. 11,352,413.

(60) Provisional application No. 62/337,388, filed on May 17, 2016.

(51) Int. Cl.

| | | |
|---|---|---|
| *C07K 14/00* | (2006.01) | |
| *A61K 38/00* | (2006.01) | |
| *C07K 14/735* | (2006.01) | |
| *C07K 14/47* | (2006.01) | |
| *C07K 14/705* | (2006.01) | |
| *A61K 38/16* | (2006.01) | |
| *A61P 31/00* | (2006.01) | |
| *A61P 35/00* | (2006.01) | |
| *A61K 38/17* | (2006.01) | |
| *C12N 15/62* | (2006.01) | |

(52) U.S. Cl.
CPC ........ *C07K 14/70535* (2013.01); *A61K 38/16* (2013.01); *A61K 38/1774* (2013.01); *A61P 31/00* (2018.01); *A61P 35/00* (2018.01); *C07K 14/47* (2013.01); *C07K 14/705* (2013.01); *C07K 14/70503* (2013.01); *C07K 14/70521* (2013.01); *C12N 15/62* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 8,735,553 B1 | 5/2014 | Li et al. |
| 9,546,206 B2 | 1/2017 | Ring et al. |
| 2004/0033497 A1 | 2/2004 | Alarcon-Riquelme et al. |
| 2015/0366174 A1 | 12/2015 | Burova et al. |
| 2019/0127439 A1 | 5/2019 | Lai et al. |

FOREIGN PATENT DOCUMENTS

WO    WO-2011/109789 A2    9/2011

OTHER PUBLICATIONS

Kozlovski, R., "How to Get the Best cDNA for Gene Isolation," BiteSizeBio, available online at https://bitesizebio.com/650/how-to-get-the-best-cdna-for-gene-isolation/#:~:text=There%20are%20several%20advantages%20to,single%2C%20intron%2Dfree%20fragment, 6 pages (2015) (Year: 2015).*
Betts et al., "Chapter 14: Amino Acid Properties and Consequences of Substitutions," Bioinformatics for Geneticists: 289-316 (2003).
Blast Sequence Comparison Between SEQ ID No. 1 and GenBank Accession No. AGK83075.1 (performed on Aug. 29, 2019): (2019).
Forni et al., "A 175 Million Year History of T Cell Regulatory Molecules Reveals Widespread Selection, with Adaptive Evolution of Disease Alleles," Immunity, 38(6): 1129-1141 (2013).
GenBank Database, Accession No. AGK83075.1: 1-2 (2013).
International Search Report and Written Opinion for International Application No. PCT/US2017/031681 dated Aug. 16, 2017.
Russell Labs, "Alanine," available online at <http://www.russelllab.org/aas/Gly.html>: (2020).

* cited by examiner

*Primary Examiner* — Thea D'Ambrosio
(74) *Attorney, Agent, or Firm* — Erik A. Huestis; Thi K. Dio; Foley Hoag LLP

(57) ABSTRACT

Isolated polypeptides comprising engineered mutant PD-1 polypeptide are provided, as are fusion polypeptides comprising the mutant and methods of use thereof. Bispecific PD-L1 and PD-L2 binding mutant PD-1 polypeptides are provided. PD-L2-specific binding mutant PD-1 polypeptides are also provided.

19 Claims, 11 Drawing Sheets

Specification includes a Sequence Listing.

hPD-1      WNPPTFSPALLVVTEGDNATFTCSFSNTSESFVLNWYRMSPSNQTDKLAAFPEDRSQPGQ hPD-1      DCRFRVTQLPNGRDFHMSVVRARRNDSGTYLCGAISLAPKAQIKESLRAELRVTERRAEV hPD-1      PTAHPSPSP (SEQ ID NO:1)

Fig. 1

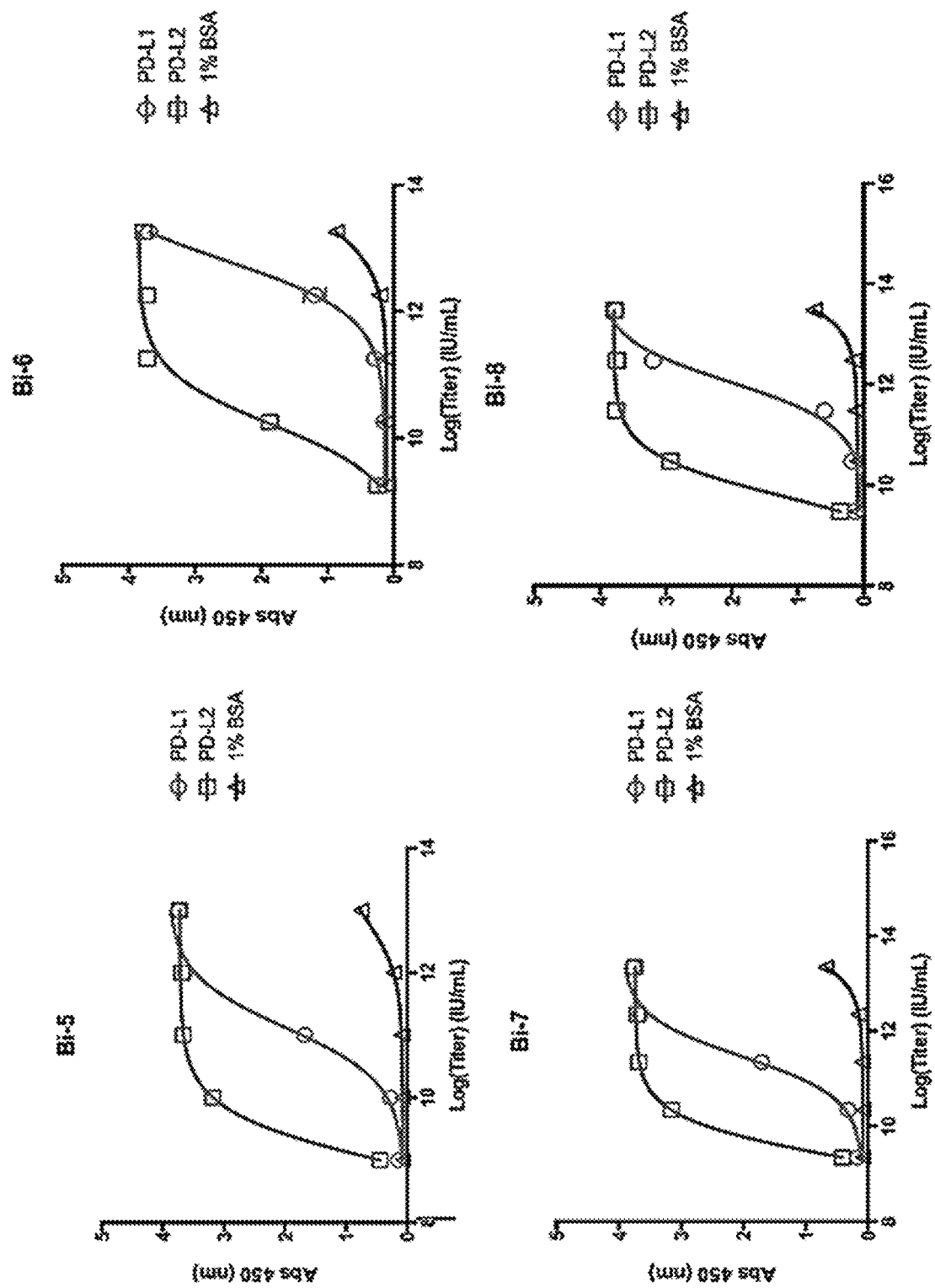
Fig. 2, Cont.

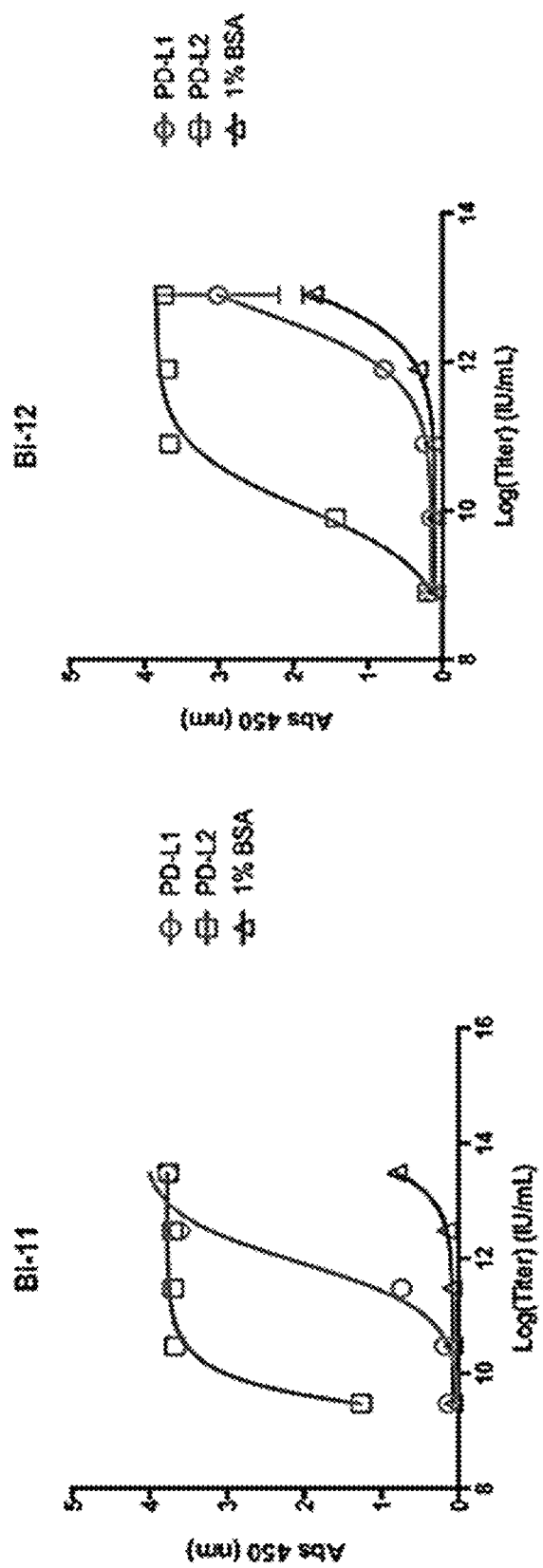
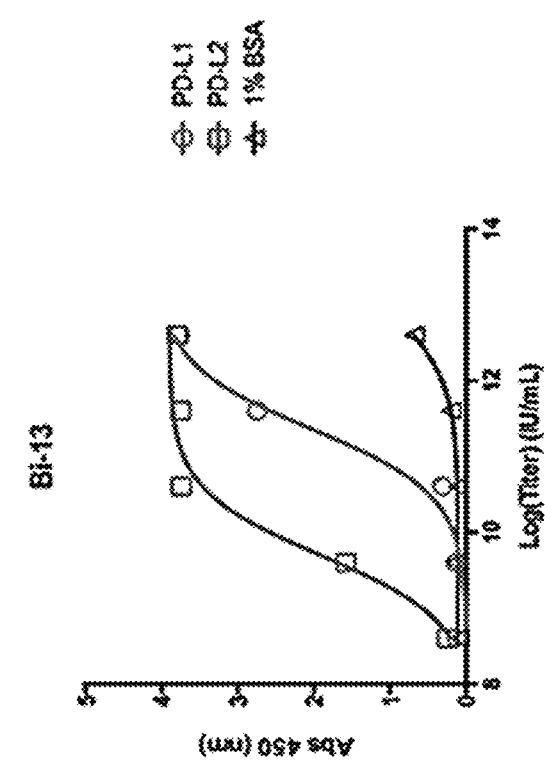
Fig. 3, Cont.

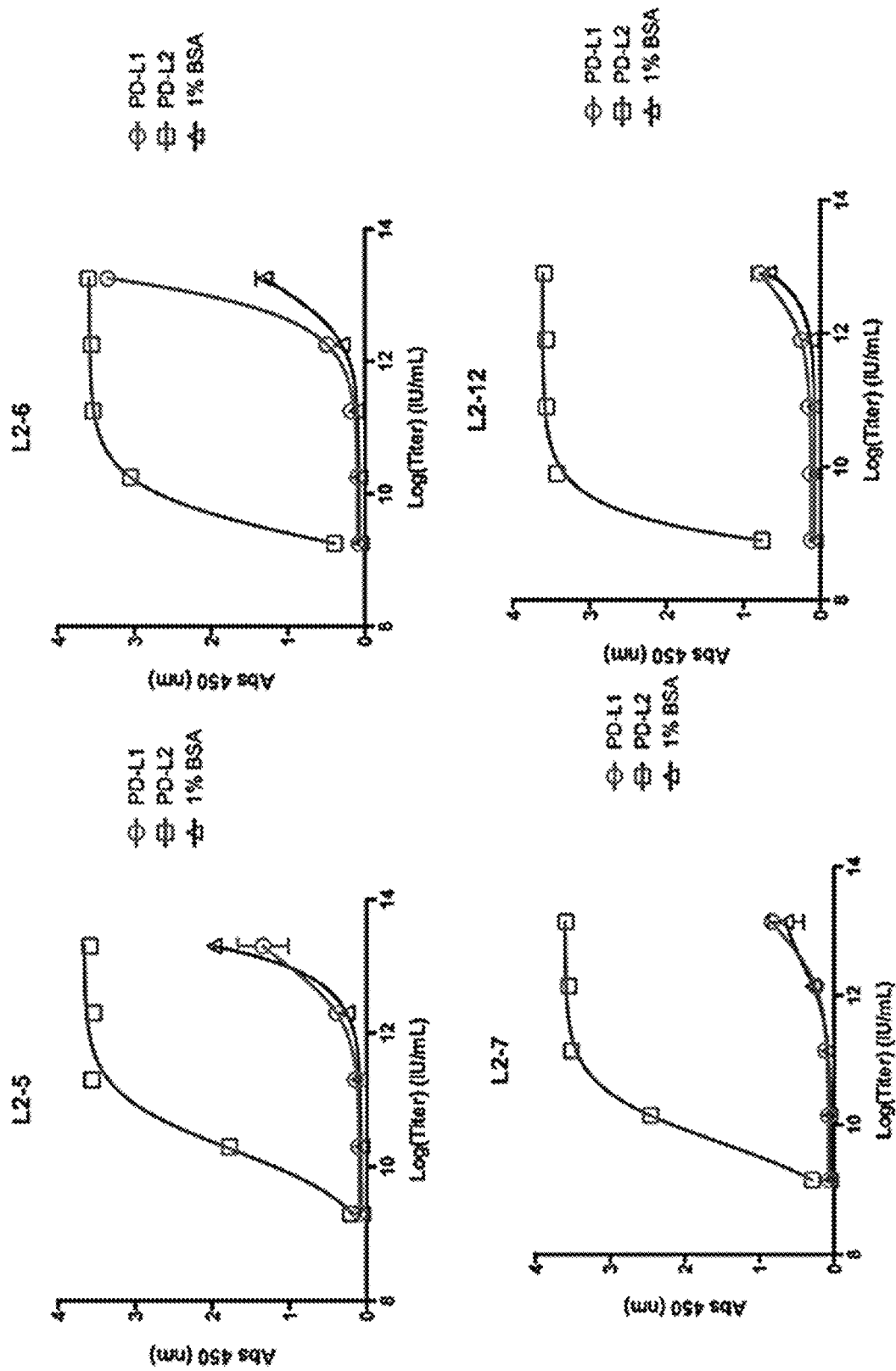
Fig. 4, Cont.

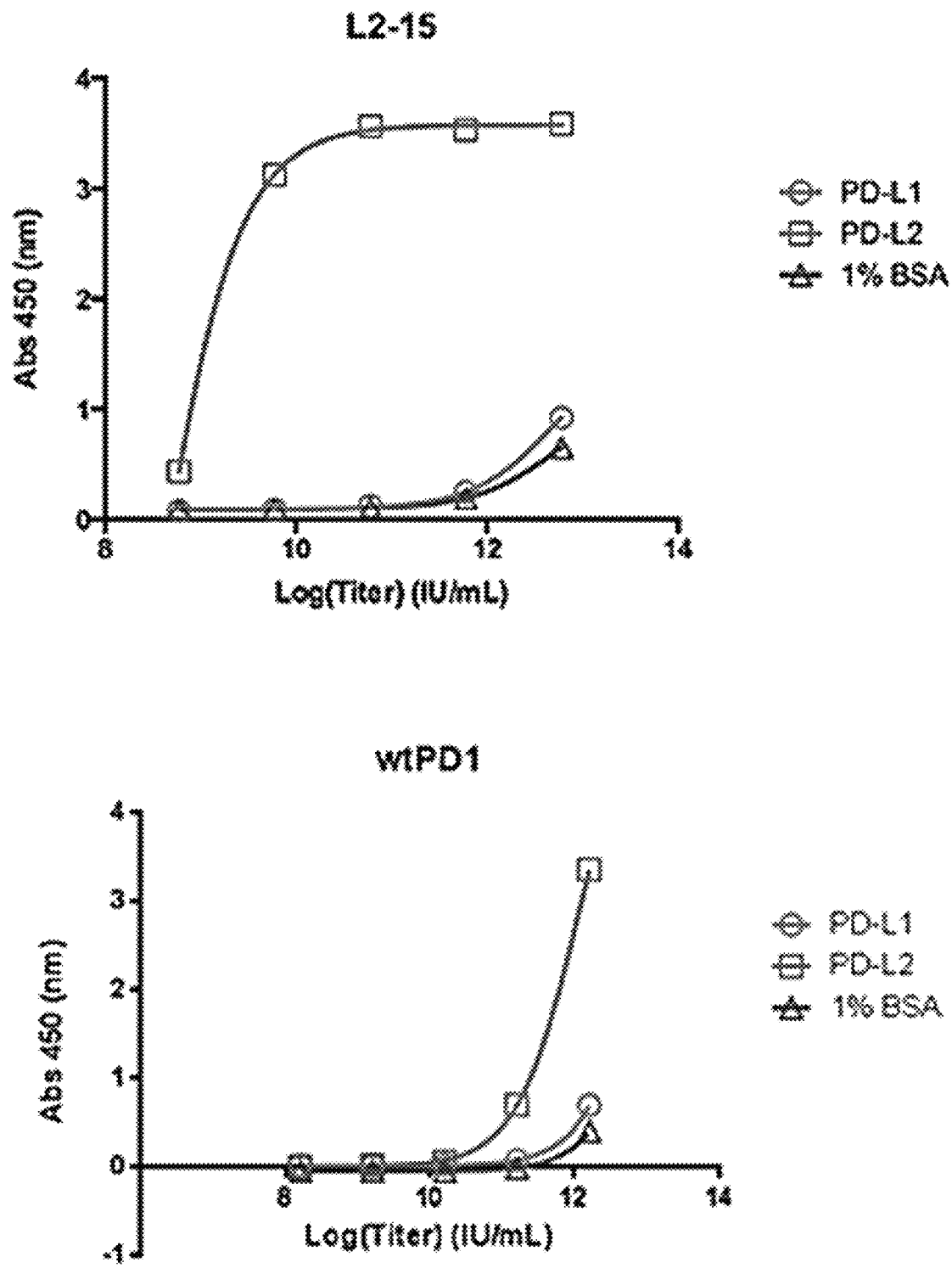
Fig. 5, Cont.

Bispecific PD-1 sequences:

```
hPD-1:WNPPTFSPALLVVTEGDNATFTCSFSNTSESFVLNWYRMSPSNQTDKLAAFPEDRSQPGQDCRFR
Bi-1:                               S V N Y LSPSNQT K    P     PG
Bi-2:                               S I N Y LSPSNQT K    P     PG
Bi-3:                               S V N Y LSPSNQT K    P     PG
Bi-4:                               S I N Y LSPSNQT K    P     PG
Bi-5:                               S V N Y LSPSNQT K    P     PG

Bi-6:                               A I N Y LSPSNQT K    P     PG
Bi-7:                               S I N Y LSASNQT K    P     PG
Bi-8:                               A I N Y LSPSNQT K    P     PG
Bi-9:                               A V N Y MSPSNQT K    P     PG
Bi-10:                              S V N Y LSPSNQT K    P     PG
Bi-11:                              S I N Y LSPSNQT K    P     PG
Bi-12:                              S I N Y MSPSNQT K    P     PG
Bi-13:                              S V N Y MSASNQT K    P     PG hPD-1: VTQLPNGRDFHMSVVRARRNDSGTYLCGAISLAPKAQIKESLRAELRVTERRAEVPTAHPSPSP
Bi-1:                           L A IALSPRA I E
Bi-2:                           L A IALSPRS I E
Bi-3:                           L A IALSPKA I E
Bi-4:                           I A IALSPRA I E
Bi-5:                           L A ISLSPRA I E
Bi-6:                           I A ISIAPRA I E
Bi-7:                           L A ISLSPKA I E
Bi-8:                           I A ISLSPRA I E
Bi-9:                           I A ISLSPKA I E
Bi-10:                          I A IALSPRA I E
Bi-11:                          I A ISLSPKA V E
Bi-12:                          I A ISLAPKS I E
Bi-13:                          I A ISLSPRA I E
```

Fig. 6

PD-L2 specific sequences:

```
hPD-1: WNPPTFSPALLVVTEGDNATFTCSFSNTSESFVLNWYRMSPSNQTDKLAAFPEDRSQPGQDCRFR
  L2-1:                             S I N Y LSPSNQT K      P     PG
  L2-2:                             S I N Y MAPSNQT K      P     PG
  L2-3:                             A V N Y MSPSNQT K      P     PG
  L2-4:                             S I N Y LSPSNQT K      P     PG
  L2-5:                             S I N Y LSPSDQT K      P     PG
  L2-6:                             S I N Y MSASNQT K      P     PG
  L2-7:                             S I N Y LSPSNQT K      P     PG
  L2-8:                             A I N Y MSASNQT K      P     PG

L2-9:                             S V N Y LSASNQT K      P     PG
  L2-10:                            S I N Y LSAANQT K      P     PG
  L2-11:                            S I N Y MSPSNQT K      P     PG
  L2-12:                            A I N Y LSPSNQT K      P     PG
  L2-13:                            A I N Y MSPSDQT K      P     PG
  L2-14:                            S I N Y MSPANQT K      P     PG
  L2-15:                            S I N Y LSPANQT K      P     PG
  L2-16:                            S I N Y MSASDQT K      P     SG

L2-17:                            A I N Y LSPSNQT K      P     PG
  L2-18:                            S I N Y MSASNQT K      P     PG
  L2-19:                            S I N Y LSASNQT K      P     PG
  L2-20:                            A I N Y LSASNQT K      P     PG
  L2-21:                            S I N Y LSASNQT K      P     PG hPD-1: VTQLPNGRDFHMSVVRARRNDSGTYLCGAISLAPKAQIKESLRAELRVTERRAEVPTAHPSPSP
  L2-1:                          I A IALSAKS V E
  L2-2:                          L A VALSPRA I E
  L2-3:                          L A IAISAKS V E
  L2-4:                          L A ISLSPRS V E
  L2-5:                          L A VSISPRS V E
  L2-6:                          L A ISLAPKA V E
  L2-7:                          L A ISLSPKS V E
  L2-8:                          L A VSLSAKS V E
  L2-9:                          L A ISISAKS V E
  L2-10:                         L A VSLSPKA V E
  L2-11:                         L A VAIAPRS V E
  L2-12:                         L A  SLSPRA V E
  L2-13:                         L A ISLSAKS I E
  L2-14:                         L A VAIAPRA V E
  L2-15:                         L A VSLAAKA V E
  L2-16:                         L A IALSAKA V E
  L2-17:                         L A ISLSAKS V E
  L2-18:                         L A VSLSPKA I E
  L2-19:                         I A ISLSARS V E
  L2-20:                         L A   IA KA V E
  L2-21:                         L A IAISARS V E
```

Fig. 7

SEQUENCE LISTING

<160> NUMBER OF SEQ ID NOS: 39

<210> SEQ ID NO 1
<211> LENGTH: 129
<212> TYPE: PRT
<213> ORGANISM: Homo sapiens

<400> SEQUENCE: 1

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Val Leu Asn Trp Tyr Arg Met Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Gly Ala Ile Ser
                85                  90                  95

Leu Ala Pro Lys Ala Gln Ile Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 2
<211> LENGTH: 129
<212> TYPE: PRT
<213> ORGANISM: Artificial Sequence
<220> FEATURE:
<223> OTHER INFORMATION: based on human PD-1
<220> FEATURE:
<221> NAME/KEY: MISC_FEATURE
<222> LOCATION: (31)..(31)
<223> OTHER INFORMATION: X = S or A
<220> FEATURE:
<221> NAME/KEY: MISC_FEATURE
<222> LOCATION: (33)..(33)
<223> OTHER INFORMATION: X = V or I
<220> FEATURE:
<221> NAME/KEY: MISC_FEATURE
<222> LOCATION: (39)..(39)
<223> OTHER INFORMATION: X = l or M
<220> FEATURE:
<221> NAME/KEY: MISC_FEATURE
<222> LOCATION: (41)..(41)
<223> OTHER INFORMATION: X = P or A
<220> FEATURE:
<221> NAME/KEY: MISC_FEATURE
<222> LOCATION: (91)..(91)
<223> OTHER INFORMATION: X = L or I
<220> FEATURE:
<221> NAME/KEY: MISC_FEATURE
<222> LOCATION: (96)..(96)
<223> OTHER INFORMATION: X = A or S
<220> FEATURE:
<221> NAME/KEY: MISC_FEATURE
<222> LOCATION: (97)..(97)
<223> OTHER INFORMATION: X = L or I
<220> FEATURE:
<221> NAME/KEY: MISC_FEATURE
<222> LOCATION: (98)..(98)
<223> OTHER INFORMATION: X = A or S
<220> FEATURE:
<221> NAME/KEY: MISC_FEATURE
<222> LOCATION: (100)..(100)
<223> OTHER INFORMATION: X = R or K

```
<220> FEATURE:
<221> NAME/KEY: MISC_FEATURE
<222> LOCATION: (101)..(101)
<223> OTHER INFORMATION: X = A or S
<220> FEATURE:
<221> NAME/KEY: MISC_FEATURE
<222> LOCATION: (103)..(103)
<223> OTHER INFORMATION: X = I or V

<400> SEQUENCE: 2

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Xaa Phe
            20                  25                  30

Xaa Leu Asn Trp Tyr Arg Xaa Ser Xaa Ser Asn Gln Thr Asp Lys Leu
        35                  40                  45

Ala Ala Phe Pro Glu Asp Arg Ser Gln Pro Gly Gln Asp Cys Arg Phe
50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Xaa Cys Ala Ala Ile Xaa
                85                  90                  95

Xaa Xaa Pro Xaa Xaa Gln Xaa Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 3
<211> LENGTH: 129
<212> TYPE: PRT
<213> ORGANISM: Artificial Sequence
<220> FEATURE:
<223> OTHER INFORMATION: based on human PD-1
<220> FEATURE:
<221> NAME/KEY: MISC_FEATURE
<222> LOCATION: (31)..(31)
<223> OTHER INFORMATION: X = S or A
<220> FEATURE:
<221> NAME/KEY: MISC_FEATURE
<222> LOCATION: (33)..(33)
<223> OTHER INFORMATION: X = V or I
<220> FEATURE:
<221> NAME/KEY: MISC_FEATURE
<222> LOCATION: (39)..(39)
<223> OTHER INFORMATION: X = L or M
<220> FEATURE:
<221> NAME/KEY: MISC_FEATURE
<222> LOCATION: (40)..(40)
<223> OTHER INFORMATION: X = S or A
<220> FEATURE:
<221> NAME/KEY: MISC_FEATURE
<222> LOCATION: (41)..(41)
<223> OTHER INFORMATION: X = P or A
<220> FEATURE:
<221> NAME/KEY: MISC_FEATURE
<222> LOCATION: (42)..(42)
<223> OTHER INFORMATION: X = S or A
<220> FEATURE:
<221> NAME/KEY: MISC_FEATURE
<222> LOCATION: (43)..(43)
<223> OTHER INFORMATION: X = N or D
<220> FEATURE:
<221> NAME/KEY: MISC_FEATURE
<222> LOCATION: (58)..(58)
<223> OTHER INFORMATION: X =P or S
<220> FEATURE:
<221> NAME/KEY: MISC_FEATURE
<222> LOCATION: (91)..(91)
```

-continued

```
<223> OTHER INFORMATION: X =L or I
<220> FEATURE:
<221> NAME/KEY: MISC_FEATURE
<222> LOCATION: (95)..(95)
<223> OTHER INFORMATION: X =I or V
<220> FEATURE:
<221> NAME/KEY: MISC_FEATURE
<222> LOCATION: (96)..(96)
<223> OTHER INFORMATION: X =A or S
<220> FEATURE:
<221> NAME/KEY: MISC_FEATURE
<222> LOCATION: (97)..(97)
<223> OTHER INFORMATION: X =L or I
<220> FEATURE:
<221> NAME/KEY: MISC_FEATURE
<222> LOCATION: (98)..(98)
<223> OTHER INFORMATION: X =A or S
<220> FEATURE:
<221> NAME/KEY: MISC_FEATURE
<222> LOCATION: (99)..(99)
<223> OTHER INFORMATION: X = P or A
<220> FEATURE:
<221> NAME/KEY: MISC_FEATURE
<222> LOCATION: (100)..(100)
<223> OTHER INFORMATION: X = R or K
<220> FEATURE:
<221> NAME/KEY: MISC_FEATURE
<222> LOCATION: (101)..(101)
<223> OTHER INFORMATION: X = A or S
<220> FEATURE:
<221> NAME/KEY: MISC_FEATURE
<222> LOCATION: (103)..(103)
<223> OTHER INFORMATION: X = I or V

<400> SEQUENCE: 3

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Xaa Phe
            20                  25                  30

Xaa Leu Asn Trp Tyr Arg Xaa Xaa Xaa Xaa Gln Thr Asp Lys Leu
        35                  40                  45

Ala Ala Phe Pro Glu Asp Arg Ser Gln Xaa Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Xaa Cys Ala Ala Xaa Xaa
                85                  90                  95

Xaa Xaa Xaa Xaa Xaa Gln Xaa Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 4
<211> LENGTH: 129
<212> TYPE: PRT
<213> ORGANISM: Artificial Sequence
<220> FEATURE:
<223> OTHER INFORMATION: based on human PD-1

<400> SEQUENCE: 4

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Val Leu Asn Trp Tyr Arg Leu Ser Pro Ser Asn Gln Thr Asp Lys Leu
```

35                  40                  45
Ala Ala Phe Pro Glu Asp Arg Ser Gln Pro Gly Gln Asp Cys Arg Phe
        50                  55                  60

Arg Val Thr Gln Leu Pro Asn Gly Arg Asp Phe His Met Ser Val Val
 65                  70                  75                  80

Arg Ala Arg Arg Asn Asp Ser Gly Thr Tyr Leu Cys Ala Ala Ile Ala
                85                  90                  95

Leu Ser Pro Arg Ala Gln Ile Lys Glu Ser Leu Arg Ala Glu Leu Arg
            100                 105                 110

Val Thr Glu Arg Arg Ala Glu Val Pro Thr Ala His Pro Ser Pro Ser
            115                 120                 125

Pro

<210> SEQ ID NO 5
<211> LENGTH: 129
<212> TYPE: PRT
<213> ORGANISM: Artificial Sequence
<220> FEATURE:
<223> OTHER INFORMATION: based on human PD-1

<400> SEQUENCE: 5

Trp Asn Pro Pro Thr Phe Ser Pro Ala Leu Leu Val Val Thr Glu Gly
 1               5                  10                  15

Asp Asn Ala Thr Phe Thr Cys Ser Phe Ser Asn Thr Ser Glu Ser Phe
             20                  25                  30

Ile Leu Asn Trp Tyr Arg Leu Ser Pro Ser Asn Gln Thr Asp Lys Leu
         35                  40                  45

Ala Ala Phe Pro Glu Asp Arg Ser Gln Pro Gly Gln Asp Cys Arg Phe
        50                  55                  60

Arg Val Thr Gln Leu Pro Asn Gly Arg Asp Phe His Met Ser Val Val
 65                  70                  75                  80

Arg Ala Arg Arg Asn Asp Ser Gly Thr Tyr Leu Cys Ala Ala Ile Ala
                85                  90                  95

Leu Ala Pro Ser Ser Gln Ile Lys Glu Ser Leu Arg Ala Glu Leu Arg
            100                 105                 110

Val Thr Glu Arg Arg Ala Glu Val Pro Thr Ala His Pro Ser Pro Ser
            115                 120                 125

Pro

<210> SEQ ID NO 6
<211> LENGTH: 129
<212> TYPE: PRT
<213> ORGANISM: Artificial Sequence
<220> FEATURE:
<223> OTHER INFORMATION: based on human PD-1

<400> SEQUENCE: 6

Trp Asn Pro Pro Thr Phe Ser Pro Ala Leu Leu Val Val Thr Glu Gly
 1               5                  10                  15

Asp Asn Ala Thr Phe Thr Cys Ser Phe Ser Asn Thr Ser Glu Ser Phe
             20                  25                  30

Val Leu Asn Trp Tyr Arg Leu Ser Pro Ser Asn Gln Thr Asp Lys Leu
         35                  40                  45

Ala Ala Phe Pro Glu Asp Arg Ser Gln Pro Gly Gln Asp Cys Arg Phe
        50                  55                  60

Arg Val Thr Gln Leu Pro Asn Gly Arg Asp Phe His Met Ser Val Val
 65                  70                  75                  80

```
Arg Ala Arg Arg Asn Asp Ser Gly Thr Tyr Leu Cys Ala Ala Ile Ala
                85                  90                  95

Leu Ser Pro Lys Ala Gln Ile Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 7
<211> LENGTH: 130
<212> TYPE: PRT
<213> ORGANISM: Artificial Sequence
<220> FEATURE:
<223> OTHER INFORMATION: based on human PD-1

<400> SEQUENCE: 7

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Ile Leu Asn Trp Tyr Arg Leu Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Ile Ala Gly Ala Ile Ala
                85                  90                  95

Leu Ser Pro Glx Arg Ala Gln Ile Lys Glu Ser Leu Arg Ala Glu Leu
            100                 105                 110

Arg Val Thr Glu Arg Arg Ala Glu Val Pro Thr Ala His Pro Ser Pro
        115                 120                 125

Ser Pro
    130

<210> SEQ ID NO 8
<211> LENGTH: 129
<212> TYPE: PRT
<213> ORGANISM: Artificial Sequence
<220> FEATURE:
<223> OTHER INFORMATION: based on human PD-1

<400> SEQUENCE: 8

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Val Leu Asn Trp Tyr Arg Leu Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Ala Ala Ile Ser
                85                  90                  95

Leu Ser Pro Arg Ala Gln Ile Lys Glu Ser Leu Arg Ala Glu Leu Arg
            100                 105                 110
```

```
Val Thr Glu Arg Arg Ala Glu Val Pro Thr Ala His Pro Ser Pro Ser
        115                 120                 125

Pro
```

<210> SEQ ID NO 9
<211> LENGTH: 129
<212> TYPE: PRT
<213> ORGANISM: Artificial Sequence
<220> FEATURE:
<223> OTHER INFORMATION: based on human PD-1

<400> SEQUENCE: 9

```
Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ala Phe
            20                  25                  30

Ile Leu Asn Trp Tyr Arg Leu Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Ile Cys Ala Ala Ile Ser
                85                  90                  95

Ile Ala Pro Arg Ala Gln Ile Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro
```

<210> SEQ ID NO 10
<211> LENGTH: 129
<212> TYPE: PRT
<213> ORGANISM: Artificial Sequence
<220> FEATURE:
<223> OTHER INFORMATION: based on humna PD-1

<400> SEQUENCE: 10

```
Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Ile Leu Asn Trp Tyr Arg Leu Ser Ala Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Ile Cys Ala Ala Ile Ser
                85                  90                  95

Ile Ala Pro Arg Ala Gln Ile Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro
```

-continued

```
<210> SEQ ID NO 11
<211> LENGTH: 129
<212> TYPE: PRT
<213> ORGANISM: Artificial Sequence
<220> FEATURE:
<223> OTHER INFORMATION: based on human PD-1

<400> SEQUENCE: 11

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ala Phe
            20                  25                  30

Ile Leu Asn Trp Tyr Arg Leu Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Ile Cys Ala Ala Ile Ser
                85                  90                  95

Leu Ser Pro Arg Ala Gln Ile Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 12
<211> LENGTH: 129
<212> TYPE: PRT
<213> ORGANISM: Artificial Sequence
<220> FEATURE:
<223> OTHER INFORMATION: based on human PD-1

<400> SEQUENCE: 12

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ala Phe
            20                  25                  30

Val Leu Asn Trp Tyr Arg Met Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Ile Cys Ala Ala Ile Ser
                85                  90                  95

Leu Ser Pro Lys Ala Gln Ile Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 13
<211> LENGTH: 129
<212> TYPE: PRT
<213> ORGANISM: Artificial Sequence
<220> FEATURE:
<223> OTHER INFORMATION: based on human PD-1
```

<400> SEQUENCE: 13

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Val Leu Asn Trp Tyr Arg Leu Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Ile Cys Ala Ala Ile Ala
                85                  90                  95

Leu Ser Pro Arg Ala Gln Ile Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 14
<211> LENGTH: 129
<212> TYPE: PRT
<213> ORGANISM: Artificial Sequence
<220> FEATURE:
<223> OTHER INFORMATION: based on human PD-1

<400> SEQUENCE: 14

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Ile Leu Asn Trp Tyr Arg Leu Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Ile Cys Ala Ala Ile Ser
                85                  90                  95

Leu Ser Pro Lys Ala Gln Val Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 15
<211> LENGTH: 129
<212> TYPE: PRT
<213> ORGANISM: Artificial Sequence
<220> FEATURE:
<223> OTHER INFORMATION: based on human PD-1

<400> SEQUENCE: 15

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Ile Leu Asn Trp Tyr Arg Met Ser Pro Ser Asn Gln Thr Asp Lys Leu
                35                  40                  45

Ala Ala Phe Pro Glu Asp Arg Ser Gln Pro Gly Gln Asp Cys Arg Phe
     50                  55                  60

Arg Val Thr Gln Leu Pro Asn Gly Arg Asp Phe His Met Ser Val Val
 65                  70                  75                  80

Arg Ala Arg Arg Asn Asp Ser Gly Thr Tyr Ile Cys Ala Ala Ile Ser
                 85                  90                  95

Leu Ala Pro Lys Ser Gln Ile Lys Glu Ser Leu Arg Ala Glu Leu Arg
                100                 105                 110

Val Thr Glu Arg Arg Ala Glu Val Pro Thr Ala His Pro Ser Pro Ser
            115                 120                 125

Pro

<210> SEQ ID NO 16
<211> LENGTH: 129
<212> TYPE: PRT
<213> ORGANISM: Artificial Sequence
<220> FEATURE:
<223> OTHER INFORMATION: based on human PD-1

<400> SEQUENCE: 16

Trp Asn Pro Pro Thr Phe Ser Pro Ala Leu Leu Val Val Thr Glu Gly
 1               5                  10                  15

Asp Asn Ala Thr Phe Thr Cys Ser Phe Ser Asn Thr Ser Glu Ser Phe
                 20                  25                  30

Val Leu Asn Trp Tyr Arg Met Ser Ala Ser Asn Gln Thr Asp Lys Leu
                35                  40                  45

Ala Ala Phe Pro Glu Asp Arg Ser Gln Pro Gly Gln Asp Cys Arg Phe
     50                  55                  60

Arg Val Thr Gln Leu Pro Asn Gly Arg Asp Phe His Met Ser Val Val
 65                  70                  75                  80

Arg Ala Arg Arg Asn Asp Ser Gly Thr Tyr Ile Cys Ala Ala Ile Ser
                 85                  90                  95

Leu Ser Pro Arg Ala Gln Ile Lys Glu Ser Leu Arg Ala Glu Leu Arg
                100                 105                 110

Val Thr Glu Arg Arg Ala Glu Val Pro Thr Ala His Pro Ser Pro Ser
            115                 120                 125

Pro

<210> SEQ ID NO 17
<211> LENGTH: 129
<212> TYPE: PRT
<213> ORGANISM: Artificial Sequence
<220> FEATURE:
<223> OTHER INFORMATION: based on human PD-1

<400> SEQUENCE: 17

Trp Asn Pro Pro Thr Phe Ser Pro Ala Leu Leu Val Val Thr Glu Gly
 1               5                  10                  15

Asp Asn Ala Thr Phe Thr Cys Ser Phe Ser Asn Thr Ser Glu Ser Phe
                 20                  25                  30

Ile Leu Asn Trp Tyr Arg Leu Ser Pro Ser Asn Gln Thr Asp Lys Leu
                35                  40                  45

Ala Ala Phe Pro Glu Asp Arg Ser Gln Pro Gly Gln Asp Cys Arg Phe
     50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Ile Cys Ala Ala Ile Ala
                85                  90                  95

Leu Ser Pro Lys Ala Gln Val Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 18
<211> LENGTH: 129
<212> TYPE: PRT
<213> ORGANISM: Artificial Sequence
<220> FEATURE:
<223> OTHER INFORMATION: based on human PD-1

<400> SEQUENCE: 18

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Ile Leu Asn Trp Tyr Arg Leu Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Ala Ala Val Ala
                85                  90                  95

Leu Ala Pro Arg Ala Gln Ile Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 19
<211> LENGTH: 129
<212> TYPE: PRT
<213> ORGANISM: Artificial Sequence
<220> FEATURE:
<223> OTHER INFORMATION: based on human PD-1

<400> SEQUENCE: 19

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ala Phe
            20                  25                  30

Val Leu Asn Trp Tyr Arg Met Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Ala Ala Ile Ala
                85                  90                  95

Ile Ser Pro Lys Ser Gln Val Lys Glu Ser Leu Arg Ala Glu Leu Arg

```
              100                 105                 110
Val Thr Glu Arg Arg Ala Glu Val Pro Thr Ala His Pro Ser Pro Ser
        115                 120                 125

Pro

<210> SEQ ID NO 20
<211> LENGTH: 129
<212> TYPE: PRT
<213> ORGANISM: Artificial Sequence
<220> FEATURE:
<223> OTHER INFORMATION: based on human PD-1

<400> SEQUENCE: 20

Trp Asn Pro Pro Thr Phe Ser Pro Ala Leu Leu Val Val Thr Glu Gly
1               5                  10                  15

Asp Asn Ala Thr Phe Thr Cys Ser Phe Ser Asn Thr Ser Glu Ala Phe
            20                  25                  30

Val Leu Asn Trp Tyr Arg Met Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Ala Ala Ile Ser
                85                  90                  95

Leu Ser Pro Arg Ser Gln Val Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 21
<211> LENGTH: 129
<212> TYPE: PRT
<213> ORGANISM: Artificial Sequence
<220> FEATURE:
<223> OTHER INFORMATION: based on human PD-1

<400> SEQUENCE: 21

Trp Asn Pro Pro Thr Phe Ser Pro Ala Leu Leu Val Val Thr Glu Gly
1               5                  10                  15

Asp Asn Ala Thr Phe Thr Cys Ser Phe Ser Asn Thr Ser Glu Ser Phe
            20                  25                  30

Ile Leu Asn Trp Tyr Arg Leu Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Ala Ala Val Ser
                85                  90                  95

Ile Ser Pro Arg Ser Gln Val Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro
```

<210> SEQ ID NO 22
<211> LENGTH: 129
<212> TYPE: PRT
<213> ORGANISM: Artificial Sequence
<220> FEATURE:
<223> OTHER INFORMATION: based on human PD-1

<400> SEQUENCE: 22

```
Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Ile Leu Asn Trp Tyr Arg Leu Ser Ala Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Gly Ala Ile Ser
                85                  90                  95

Leu Ala Pro Lys Ala Gln Val Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro
```

<210> SEQ ID NO 23
<211> LENGTH: 129
<212> TYPE: PRT
<213> ORGANISM: Artificial Sequence
<220> FEATURE:
<223> OTHER INFORMATION: based on human PD-1

<400> SEQUENCE: 23

```
Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Ile Leu Asn Trp Tyr Arg Leu Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Ala Ala Ile Ser
                85                  90                  95

Leu Ser Pro Lys Ser Gln Val Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro
```

<210> SEQ ID NO 24
<211> LENGTH: 129
<212> TYPE: PRT
<213> ORGANISM: Artificial Sequence
<220> FEATURE:
<223> OTHER INFORMATION: based on human PD-1

<400> SEQUENCE: 24

```
Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ala Phe
            20                  25                  30

Ile Leu Asn Trp Tyr Arg Met Ser Ala Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Ala Ala Val Ser
                85                  90                  95

Leu Ser Ala Lys Ser Gln Val Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro
```

<210> SEQ ID NO 25
<211> LENGTH: 129
<212> TYPE: PRT
<213> ORGANISM: Artificial Sequence
<220> FEATURE:
<223> OTHER INFORMATION: based on human PD-1

<400> SEQUENCE: 25

```
Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Val Leu Asn Trp Tyr Arg Leu Ser Ala Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Ala Ala Val Ser
                85                  90                  95

Leu Ser Ala Lys Ser Gln Val Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro
```

<210> SEQ ID NO 26
<211> LENGTH: 129
<212> TYPE: PRT
<213> ORGANISM: Artificial Sequence
<220> FEATURE:
<223> OTHER INFORMATION: based on human PD-1

<400> SEQUENCE: 26

```
Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
```

20                  25                  30

Ile Leu Asn Trp Tyr Arg Leu Ser Ala Ala Asn Gln Thr Asp Lys Leu
            35                  40                  45

Ala Ala Phe Pro Glu Asp Arg Ser Gln Pro Gly Gln Asp Cys Arg Phe
 50                  55                  60

Arg Val Thr Gln Leu Pro Asn Gly Arg Asp Phe His Met Ser Val Val
 65                  70                  75                  80

Arg Ala Arg Arg Asn Asp Ser Gly Thr Tyr Leu Cys Ala Ala Val Ser
                85                  90                  95

Leu Ser Pro Lys Ala Gln Val Lys Glu Ser Leu Arg Ala Glu Leu Arg
            100                 105                 110

Val Thr Glu Arg Arg Ala Glu Val Pro Thr Ala His Pro Ser Pro Ser
            115                 120                 125

Pro

<210> SEQ ID NO 27
<211> LENGTH: 129
<212> TYPE: PRT
<213> ORGANISM: Artificial Sequence
<220> FEATURE:
<223> OTHER INFORMATION: based on human PD-1

<400> SEQUENCE: 27

Trp Asn Pro Pro Thr Phe Ser Pro Ala Leu Leu Val Val Thr Glu Gly
 1               5                  10                  15

Asp Asn Ala Thr Phe Thr Cys Ser Phe Ser Asn Thr Ser Glu Ser Phe
            20                  25                  30

Ile Leu Asn Trp Tyr Arg Met Ser Pro Ser Asn Gln Thr Asp Lys Leu
            35                  40                  45

Ala Ala Phe Pro Glu Asp Arg Ser Gln Pro Gly Gln Asp Cys Arg Phe
 50                  55                  60

Arg Val Thr Gln Leu Pro Asn Gly Arg Asp Phe His Met Ser Val Val
 65                  70                  75                  80

Arg Ala Arg Arg Asn Asp Ser Gly Thr Tyr Leu Cys Ala Ala Val Ala
                85                  90                  95

Ile Ala Pro Arg Ser Gln Val Lys Glu Ser Leu Arg Ala Glu Leu Arg
            100                 105                 110

Val Thr Glu Arg Arg Ala Glu Val Pro Thr Ala His Pro Ser Pro Ser
            115                 120                 125

Pro

<210> SEQ ID NO 28
<211> LENGTH: 128
<212> TYPE: PRT
<213> ORGANISM: Artificial Sequence
<220> FEATURE:
<223> OTHER INFORMATION: based on human PD-1

<400> SEQUENCE: 28

Trp Asn Pro Pro Thr Phe Ser Pro Ala Leu Leu Val Val Thr Glu Gly
 1               5                  10                  15

Asp Asn Ala Thr Phe Thr Cys Ser Phe Ser Asn Thr Ser Glu Ala Phe
            20                  25                  30

Ile Leu Asn Trp Tyr Arg Leu Ser Pro Ser Asn Gln Thr Asp Lys Leu
            35                  40                  45

Ala Ala Phe Pro Glu Asp Arg Ser Gln Pro Gly Gln Asp Cys Arg Phe
 50                  55                  60

```
Arg Val Thr Gln Leu Pro Asn Gly Arg Asp Phe His Met Ser Val Val
 65                  70                  75                  80

Arg Ala Arg Arg Asn Asp Ser Gly Thr Tyr Leu Cys Ala Ala Ser Leu
                 85                  90                  95

Ser Pro Arg Ala Gln Val Lys Glu Ser Leu Arg Ala Glu Leu Arg Val
            100                 105                 110

Thr Glu Arg Arg Ala Glu Val Pro Thr Ala His Pro Ser Pro Ser Pro
        115                 120                 125
```

<210> SEQ ID NO 29
<211> LENGTH: 129
<212> TYPE: PRT
<213> ORGANISM: Artificial Sequence
<220> FEATURE:
<223> OTHER INFORMATION: based on human PD-1

<400> SEQUENCE: 29

```
Trp Asn Pro Pro Thr Phe Ser Pro Ala Leu Leu Val Val Thr Glu Gly
  1               5                  10                  15

Asp Asn Ala Thr Phe Thr Cys Ser Phe Ser Asn Thr Ser Glu Ala Phe
                 20                  25                  30

Ile Leu Asn Trp Tyr Arg Met Ser Pro Ser Asp Gln Thr Asp Lys Leu
             35                  40                  45

Ala Ala Phe Pro Glu Asp Arg Ser Gln Pro Gly Gln Asp Cys Arg Phe
 50                  55                  60

Arg Val Thr Gln Leu Pro Asn Gly Arg Asp Phe His Met Ser Val Val
 65                  70                  75                  80

Arg Ala Arg Arg Asn Asp Ser Gly Thr Tyr Leu Cys Ala Ala Ile Ser
                 85                  90                  95

Leu Ser Ala Lys Ser Gln Ile Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro
```

<210> SEQ ID NO 30
<211> LENGTH: 129
<212> TYPE: PRT
<213> ORGANISM: Artificial Sequence
<220> FEATURE:
<223> OTHER INFORMATION: based on human PD-1

<400> SEQUENCE: 30

```
Trp Asn Pro Pro Thr Phe Ser Pro Ala Leu Leu Val Val Thr Glu Gly
  1               5                  10                  15

Asp Asn Ala Thr Phe Thr Cys Ser Phe Ser Asn Thr Ser Glu Ser Phe
                 20                  25                  30

Ile Leu Asn Trp Tyr Arg Met Ser Pro Ser Asn Gln Thr Asp Lys Leu
             35                  40                  45

Ala Ala Phe Pro Glu Asp Arg Ser Gln Pro Gly Gln Asp Cys Arg Phe
 50                  55                  60

Arg Val Thr Gln Leu Pro Asn Gly Arg Asp Phe His Met Ser Val Val
 65                  70                  75                  80

Arg Ala Arg Arg Asn Asp Ser Gly Thr Tyr Leu Cys Ala Ala Val Ala
                 85                  90                  95

Ile Ala Pro Arg Ala Gln Val Lys Glu Ser Leu Arg Ala Glu Leu Arg
            100                 105                 110
```

```
Val Thr Glu Arg Arg Ala Glu Val Pro Thr Ala His Pro Ser Pro Ser
        115                 120                 125

Pro
```

<210> SEQ ID NO 31
<211> LENGTH: 129
<212> TYPE: PRT
<213> ORGANISM: Artificial Sequence
<220> FEATURE:
<223> OTHER INFORMATION: based on human PD-1

<400> SEQUENCE: 31

```
Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Ile Leu Asn Trp Tyr Arg Leu Ser Pro Ala Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Ala Ala Val Ser
                85                  90                  95

Leu Ala Ala Lys Ala Gln Val Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro
```

<210> SEQ ID NO 32
<211> LENGTH: 129
<212> TYPE: PRT
<213> ORGANISM: Artificial Sequence
<220> FEATURE:
<223> OTHER INFORMATION: based on human PD-1

<400> SEQUENCE: 32

```
Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Ile Leu Asn Trp Tyr Arg Met Ser Ala Ser Asp Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Ala Ala Ile Ala
                85                  90                  95

Leu Ser Ala Lys Ala Gln Val Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro
```

```
<210> SEQ ID NO 33
<211> LENGTH: 129
<212> TYPE: PRT
<213> ORGANISM: Artificial Sequence
<220> FEATURE:
<223> OTHER INFORMATION: based on human PD-1

<400> SEQUENCE: 33

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ala Phe
            20                  25                  30

Ile Leu Asn Trp Tyr Arg Leu Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Ala Ala Ile Ser
                85                  90                  95

Leu Ser Ala Lys Ser Gln Val Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 34
<211> LENGTH: 129
<212> TYPE: PRT
<213> ORGANISM: Artificial Sequence
<220> FEATURE:
<223> OTHER INFORMATION: based on human PD-1

<400> SEQUENCE: 34

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ala Phe
            20                  25                  30

Ile Leu Asn Trp Tyr Arg Leu Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Ala Ala Val Ser
                85                  90                  95

Leu Ser Pro Lys Ala Gln Ile Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 35
<211> LENGTH: 129
<212> TYPE: PRT
<213> ORGANISM: Artificial Sequence
<220> FEATURE:
<223> OTHER INFORMATION: based on human PD-1
```

<400> SEQUENCE: 35

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Ile Leu Asn Trp Tyr Arg Leu Ser Ala Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Ile Cys Ala Ala Ile Ser
                85                  90                  95

Leu Ser Ala Arg Ser Gln Val Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 36
<211> LENGTH: 126
<212> TYPE: PRT
<213> ORGANISM: Artificial Sequence
<220> FEATURE:
<223> OTHER INFORMATION: based on human PD-1

<400> SEQUENCE: 36

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ala Phe
            20                  25                  30

Ile Leu Asn Trp Tyr Arg Leu Ser Ala Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Ala Ala Ile Ala
                85                  90                  95

Lys Ala Gln Val Lys Glu Ser Leu Arg Ala Glu Leu Arg Val Thr Glu
            100                 105                 110

Arg Arg Ala Glu Val Pro Thr Ala His Pro Ser Pro Ser Pro
        115                 120                 125

<210> SEQ ID NO 37
<211> LENGTH: 129
<212> TYPE: PRT
<213> ORGANISM: Artificial Sequence
<220> FEATURE:
<223> OTHER INFORMATION: based on human PD-1

<400> SEQUENCE: 37

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Ile Leu Asn Trp Tyr Arg Leu Ser Ala Ser Asn Gln Thr Asp Lys Leu

```
                    35                  40                  45
Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Ala Ala Ile Ala
                85                  90                  95

Ile Ser Ala Arg Ser Gln Val Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro

<210> SEQ ID NO 38
<211> LENGTH: 5
<212> TYPE: PRT
<213> ORGANISM: Artificial Sequence
<220> FEATURE:
<223> OTHER INFORMATION: synthetic linker

<400> SEQUENCE: 38

Gly Gly Gly Gly Ser
1               5

<210> SEQ ID NO 39
<211> LENGTH: 5
<212> TYPE: PRT
<213> ORGANISM: Artificial Sequence
<220> FEATURE:
<223> OTHER INFORMATION: synthetic linker

<400> SEQUENCE: 39

Glu Ala Ala Ala Lys
1               5
```

ENGINEERED PD-1 VARIANTS

CROSS-REFERENCE TO RELATED APPLICATIONS

This application is a continuation application of U.S. Serial Application No. 16/096,369, filed on Oct. 25, 2018, which is a U.S. national stage entry under 35 U.S.C. § 371 of PCT International Patent Application No. PCT/US17/31681, filed on May 9, 2017, which claims benefit of U.S. Provisional Application No. 62/337,388, filed May 17, 2016, the contents of each of which are hereby incorporated in their entirety by this reference.

SEQUENCE LISTING

The instant application contains a Sequence Listing which has been submitted in ASCII format via EFS-Web and is hereby incorporated by reference in its entirety. Said ASCII copy, created on Aug. 5, 2020, is named AET-00601_ST25.txt and is 46.4 KB in size.

BACKGROUND OF THE INVENTION

Throughout this application various publications are referred to. The disclosures of these publications, and of all patents, patent application publications and books referred to herein, are hereby incorporated by reference in their entirety into the subject application to more fully describe the art to which the subject invention pertains.

In recent years, T cell costimulatory pathways have been identified as versatile novel targets for immunotherapeutic strategies. The CD28:B7 family of T cell costimulatory molecules includes CD28 and ICOS as positive co-receptors, and CTLA4 and PD-1 as co-inhibitors, which tightly regulate all T cell activation processes.

Enhancing T cell activation by blockade of the PD-L/PD-1 inhibitory pathway has enormous potential for the treatment of infectious diseases and malignant tumors. Recent studies have shown that enhancing T cell activation by blocking PD-1 could be beneficial in chronic viral infections, as well as other infections in which this costimulatory pathway is involved. Host responses to pathogens such as fungi, protozoa, worms and bacteria have been shown to be regulated by PD-1, and therefore could be improved by manipulating the PD-1 pathway.

Although targeting costimulatory pathways is a relatively recent approach, there are a number of antibodies approved for clinical use and myriad others in development for clinical trials. One such FDA-approved drug is Yervoy (Ipilimumab), which is a monoclonal antibody directed against the co-inhibitory receptor CTLA-4. Yervoy has been shown to be effective in increasing survival of metastatic melanoma patients (10 months median survival for the antibody treated group versus 6.4 months for the control group, Hodi F S et al, N Engl J Med 2010). Yervoy acts through inducing activation of T cells by blocking CTLA-4, causing significant immune stimulation, including anti-tumor immune responses. Due to the central role of CTLA-4 in all immune responses (central and peripheral), Yervoy can cause significant side effects associated with an overly active immune response, e.g. autoimmune symptoms can develop and in some cases these can be lethal. Notably, the absence of CTLA-4 in mice caused by genetic deletion is lethal, highlighting the importance of this molecular "brake" on the general immune response. Furthermore, the FDA recently granted accelerated approval for Keytruda (pembrolizumab) which is a monoclonal antibody directed against PD-1 to treat patients with advanced (metastatic) non-small cell lung cancer (NSCLC) whose disease has progressed after other treatments failed, and for tumors that express a PD-1 ligand protein called PD-L1. Keytruda is also approved for use with a companion diagnostic. Many other PD-1 and PD-L1 targeting antibodies are under clinical and preclinical development.

The present invention addresses the need for improved targeting of costimulatory pathways by manipulating the PD-1 pathway and provides high affinity PD-1-based immune stimulatory agents.

SUMMARY OF THE INVENTION

This invention provides an isolated polypeptide comprising a mutant PD-1 polypeptide having the sequence (i) SEQ ID NO:2, or (ii) SEQ ID NO:3, or (iii) having a sequence at least 95% identical to SEQ ID NO:2 or SEQ ID NO:3 with the proviso that the sequence at least 95% identical to SEQ ID NO:2 or SEQ ID NO:3 is not SEQ ID NO:1.

This invention provides an isolated polypeptide comprising a mutant PD-1 polypeptide comprising SEQ ID NO:2 or SEQ ID NO:3, wherein the mutant PD-1 polypeptide is a mutant by having a mutation relative to NCBI Reference Sequence NP_005009.2 or to SEQ ID NO:1.

This invention also provides a fusion polypeptide comprising a mutant PD-1 polypeptide (or engineered PD-1) described herein, fused to an immunoglobulin domain polypeptide.

This invention also provides a homo-oligomer comprising the isolated polypeptide comprising a mutant PD-1 polypeptide described herein, or comprising the fusion polypeptide. In a preferred embodiment, the homo-oligomer comprises two of the isolated polypeptides, or two of the fusion polypeptides.

This invention also provides a composition comprising the isolated mutant PD-1 polypeptide in monovalent form or oligomeric form. This invention also provides a composition comprising the fusion polypeptide comprising the mutant PD-1 in monovalent form or oligomeric form.

Also provided is a method of stimulating T cell activation in a subject comprising administering to the subject the isolated mutant PD-1 polypeptide described herein, or the composition or homo-oligomer comprising the isolated mutant PD-1 polypeptide described herein, in an amount sufficient to stimulate T cell activation in a subject.

Also provided is a method of stimulating T cell activation in a subject comprising administering to the subject the isolated fusion polypeptide comprising the mutant PD-1 described herein, or the composition or homo-oligomer comprising the isolated fusion polypeptide comprising the mutant PD-1 described herein, in an amount sufficient to stimulate T cell activation in a subject.

Also provided is a method of treating a tumor, or treating an infection, in a subject comprising administering to the subject the isolated mutant PD-1 polypeptide described herein, or the composition or homo-oligomer comprising the isolated mutant PD-1 polypeptide described herein, in an amount sufficient to stimulate T cell activation, treat a tumor, or treat an infection, respectively, in a subject.

Also provided is a method of treating a tumor, or treating an infection, in a subject comprising administering to the subject the isolated fusion polypeptide comprising the mutant PD-1 described herein, or the composition or homo-oligomer comprising the isolated fusion polypeptide comprising the mutant PD-1 described herein, in an amount sufficient to stimulate T cell activation, treat a tumor, or treat an infection, respectively, in a subject.

BRIEF DESCRIPTION OF THE DRAWINGS

FIG. 1: Human PD-1 (SEQ ID NO:1) engineered variants design. The designed library allows limited variation at the underlined residues.

FIG. 6: Bispecific (PD-L1 and PD-L2) engineered mutant PD-1 sequences. (Sequences split into two sections for visual display due to length of sequences). hPD-1 is SEQ ID NO:1; Bi-1 is SEQ ID NO:4; Bi-2 is SEQ ID NO:5; Bi-3 is SEQ ID NO:6; Bi-4 is SEQ ID NO:7; Bi-5 is SEQ ID NO:8; Bi-6 is SEQ ID NO:9; Bi-7 is SEQ ID NO:10; Bi-8 is SEQ ID NO:11; Bi-9 is SEQ ID NO:12; Bi-10 is SEQ ID NO:13; Bi-11 is SEQ ID NO:14; Bi-12 is SEQ ID NO:15; and Bi-13 is SEQ ID NO:16.

FIG. 7: PD-L2-specific engineered mutant PD-1 sequences. (Sequences split into two sections for visual display due to length of sequences). hPD-1 is SEQ ID NO:1; L2-1 is SEQ ID NO:17; L2-2 is SEQ ID NO:18; L2-3 is SEQ ID NO:19; L2-4 is SEQ ID NO:20; L2-5 is SEQ ID NO:21; L2-6 is SEQ ID NO:22; L2-7 is SEQ ID NO:23; L2-8 is SEQ ID NO:24; L2-9 is SEQ ID NO:25; L2-10 is SEQ ID NO:26; L2-11 is SEQ ID NO:27; L2-12 is SEQ ID NO:28; L2-13 is SEQ ID NO:29; L2-14 is SEQ ID NO:30; L2-15 is SEQ ID NO:31; L2-16 is SEQ ID NO:32; L2-17 is SEQ ID NO:33; L2-18 is SEQ ID NO:34; L2-19 is SEQ ID NO:35; L2-20 is SEQ ID NO:36; and L2-21 is SEQ ID NO:37.

DETAILED DESCRIPTION OF THE INVENTION

An isolated mutant PD-1 polypeptide is provided comprising (i) SEQ ID NO:2, or (ii) SEQ ID NO:3, or (ii) having a sequence 95% or greater identical to SEQ ID NO:2 or SEQ ID NO:3 with the proviso that the mutant PD-1 polypeptide does not comprise SEQ ID NO:1.

An engineered PD-1 polypeptide is provided comprising (i) SEQ ID NO:2, or (ii) SEQ ID NO:3, or (ii) having a sequence 95% or greater identical to SEQ ID NO:2 or SEQ ID NO:3 with the proviso that the engineered PD-1 polypeptide does not comprise SEQ ID NO:1.

In an embodiment, the isolated mutant PD-1 polypeptide comprises SEQ ID NO:2. In an embodiment the isolated mutant PD-1 polypeptide comprises SEQ ID NO:3. In an embodiment, the isolated mutant PD-1 polypeptide consists of SEQ ID NO:2 with 1, 2, 3, 4, 5, 6, 7, 8, 9 or 10 additional amino acids at either the N-terminal, the C-terminal or, independently, at both N and C terminals. In an embodiment, the isolated mutant PD-1 polypeptide consists of SEQ ID NO:3 with 1, 2, 3, 4, 5, 6, 7, 8, 9 or 10 additional amino acids at either the N-terminal, the C-terminal or, independently, at both N and C terminals.

In an embodiment, the isolated mutant PD-1 polypeptide consists of SEQ ID NO:2 with only 1 additional amino acid at one terminal thereof and no additional amino acid at the other terminal thereof. In an embodiment, the isolated mutant PD-1 polypeptide consists of SEQ ID NO:2 with only 1 additional amino acid at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:2 with only 2 additional amino acids at one terminal thereof and no additional amino acid at the other terminal thereof. In an embodiment, the isolated mutant PD-1 polypeptide consists of SEQ ID NO:2 with only 2 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:2 with only 3 additional amino acids at one terminal thereof and no additional amino acid at the other terminal thereof. In an embodiment, the isolated mutant PD-1 polypeptide consists of SEQ ID NO:2 with only 3 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:2 with only 4 additional amino acids at one terminal thereof and no additional amino acid at the other terminal thereof. In an embodiment, the isolated mutant PD-1 polypeptide consists of SEQ ID NO:2 with only 4 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:2 with only 5 additional amino acids at one terminal thereof and no additional amino acid at the other terminal thereof. In an embodiment, the isolated mutant PD-1 polypeptide consists of SEQ ID NO:2 with only 5 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:2 with only 6 additional amino acids at one terminal thereof and no additional amino acid at the other terminal thereof. In an embodiment, the isolated mutant PD-1 polypeptide consists of SEQ ID NO:2 with only 6 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:2 with only 7 additional amino acids at one terminal thereof and no additional amino acid at the other terminal thereof. In an embodiment, the isolated mutant PD-1 polypeptide consists of SEQ ID NO:2 with only 7 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

Figure 2:
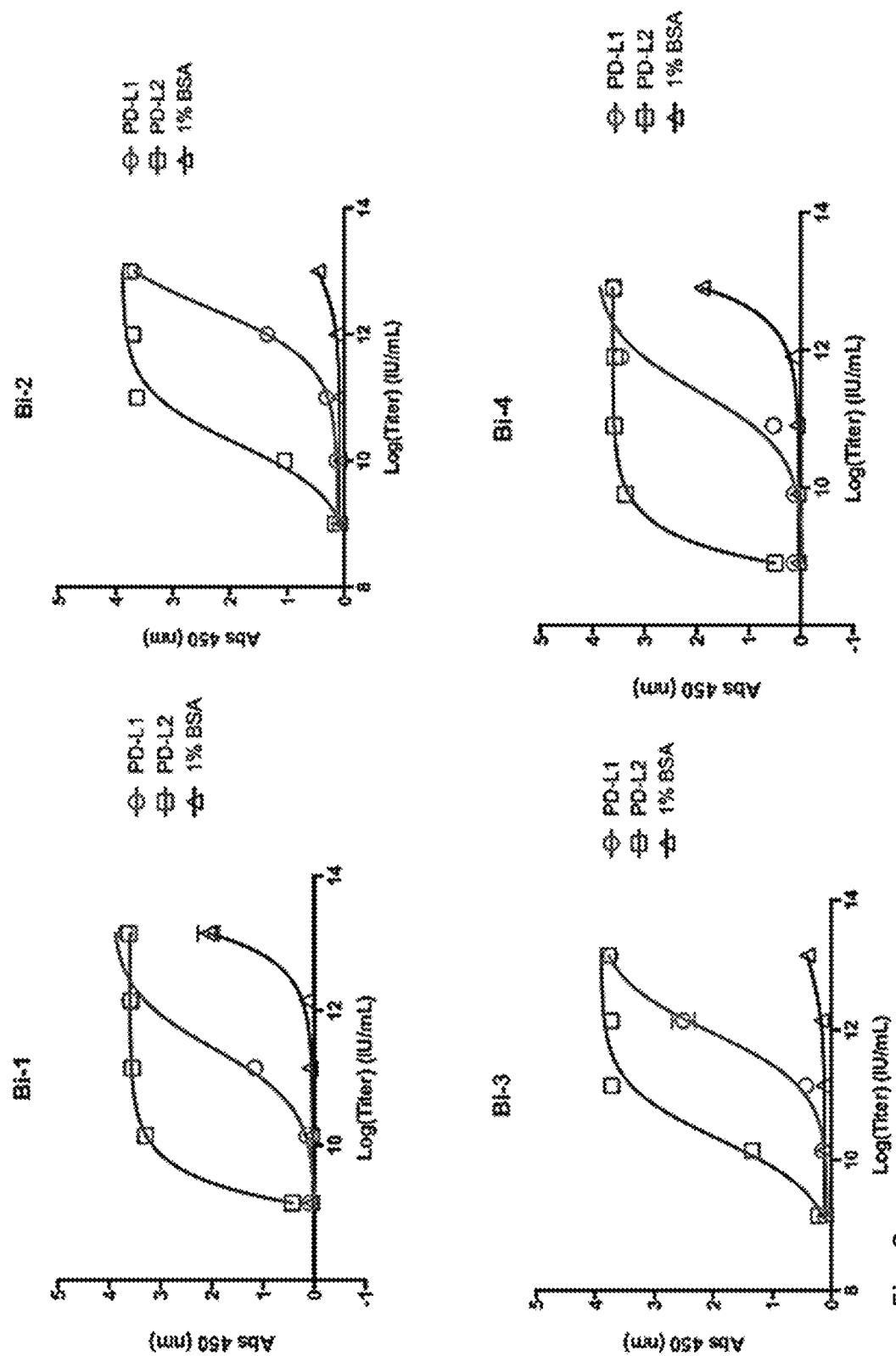
FIG. 2: Bispecific ePD-1s (bind both PD-L1 and PD-L2). Monoclonal phage ELISAs of hits from the PD-L1/PD-L2 toggle selection.
Figure 3:
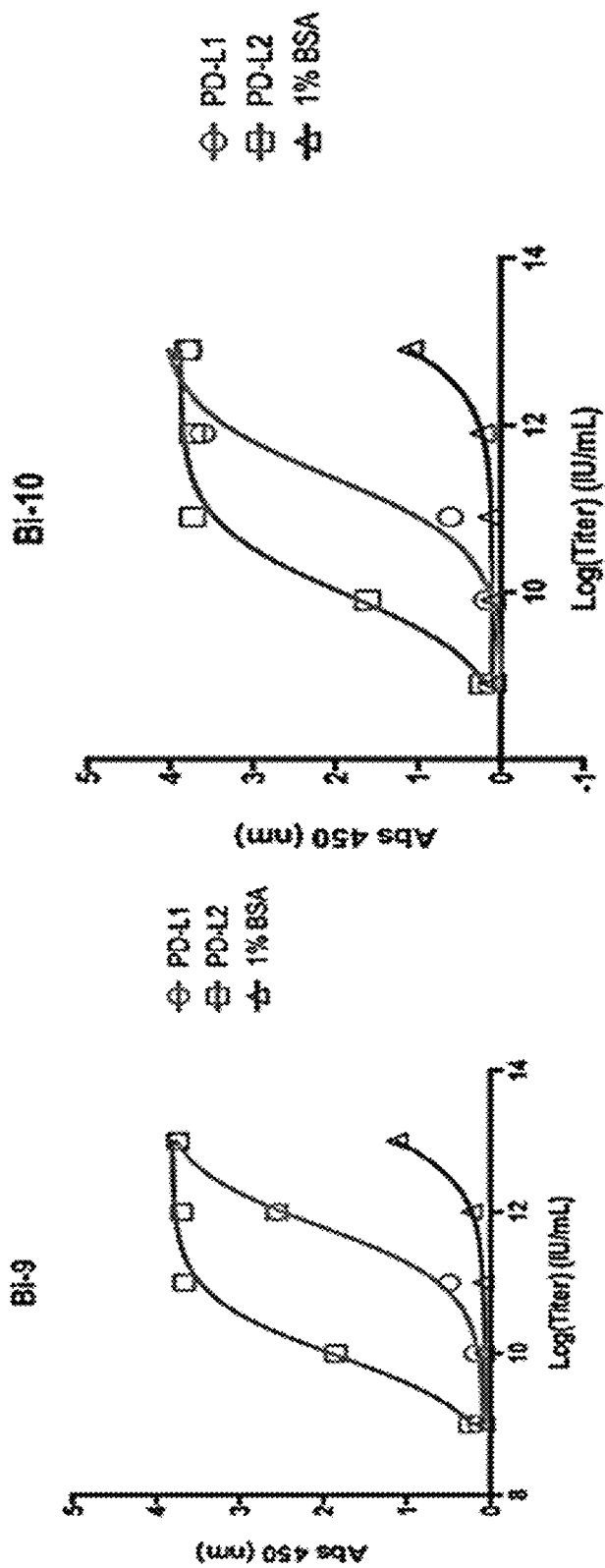
FIG. 3: Bispecific ePD-1s (bind both PD-L1 and PD-L2). Monoclonal phage ELISAs of hits from the PD-L1/PD-L2 toggle selection.
Figure 4:
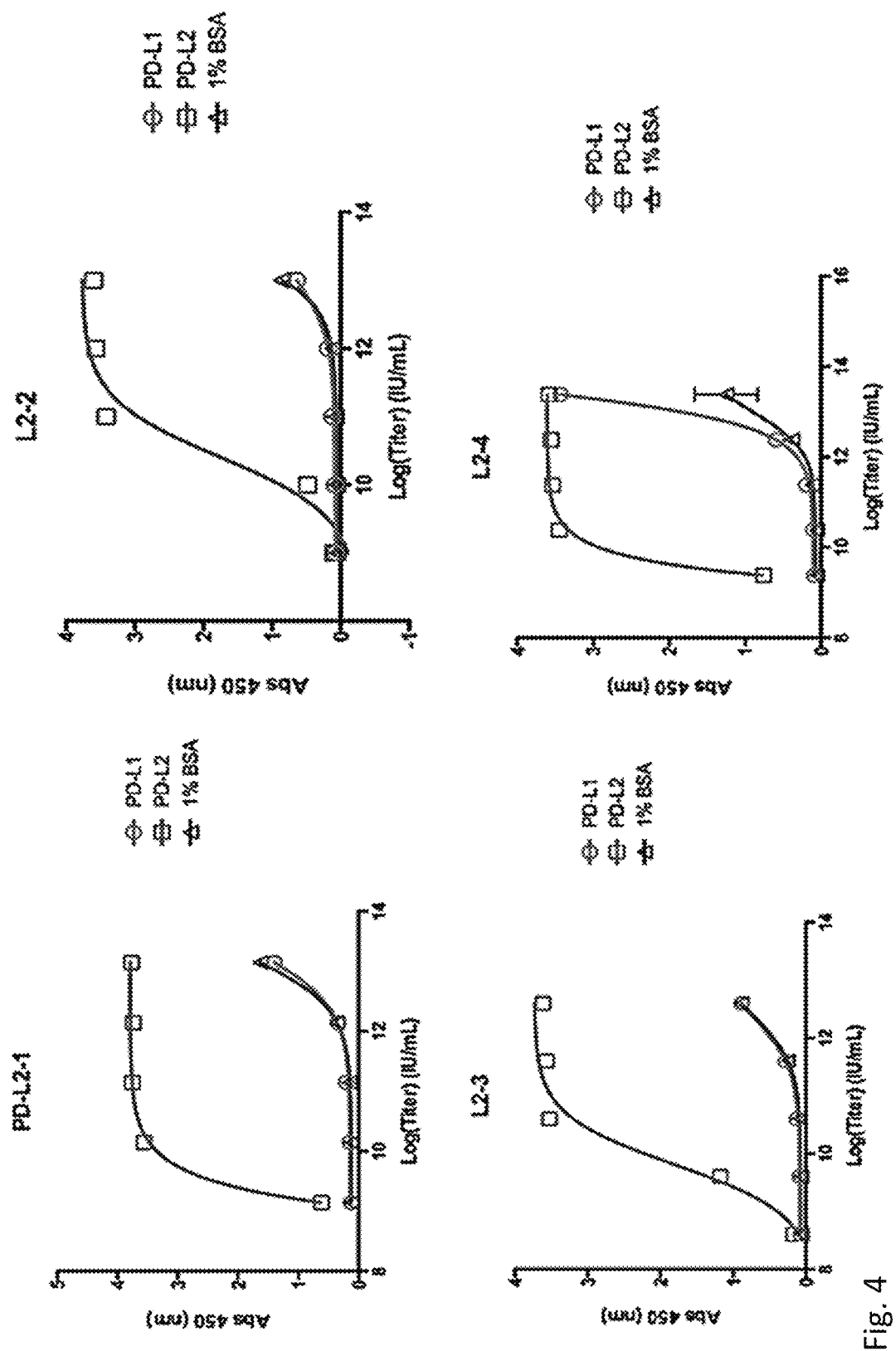
FIG. 4: PD-L2-specific ePD-1s. Monoclonal phage ELISAs of hits from the PD-L1/PD-L2 toggle selection.
Figure 5:
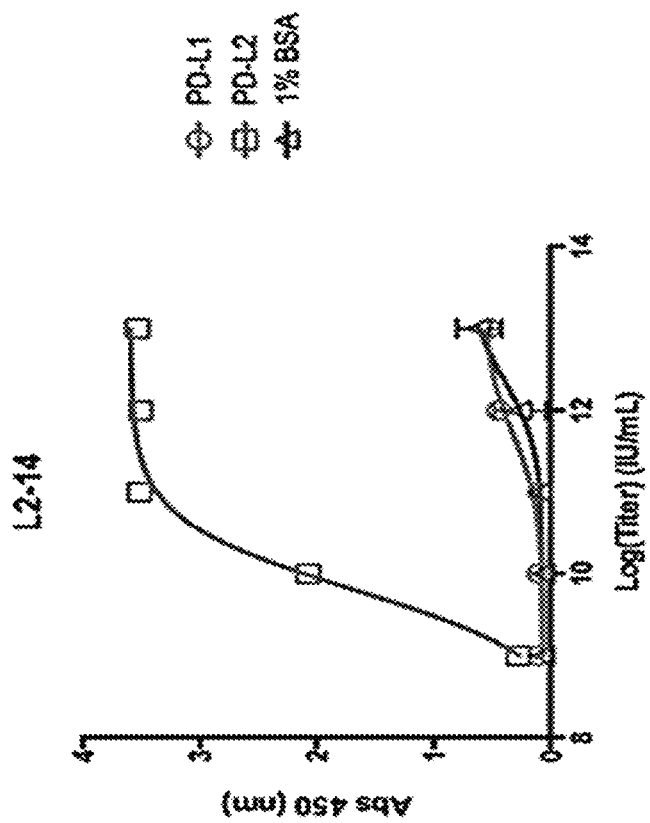
FIG. 5: PD-L2-specific ePD-1s. Monoclonal phage ELISAs of hits from the PD-L1/PD-L2 toggle selection and control WT PD1 data.
Figure 5:
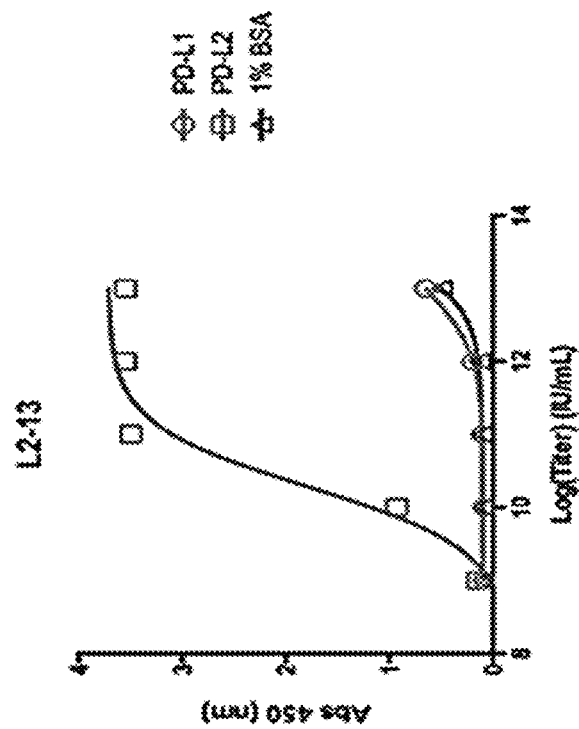

In an embodiment, the isolated mutant PD-1 polypeptide consists of SEQ ID NO:2 with only 8 additional amino acids at one terminal thereof and no additional amino acid at the other terminal thereof. In an embodiment, the isolated mutant PD-1 polypeptide consists of SEQ ID NO:2 with only 8 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:2 with only 9 additional amino acids at one terminal thereof and no additional amino acid at the other terminal thereof. In an embodiment, the isolated mutant PD-1 polypeptide consists of SEQ ID NO:2 with only 9 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:2 with only 10 additional amino acids at one terminal thereof and no additional amino acid at the other terminal thereof. In an embodiment, the isolated mutant PD-1 polypeptide consists of SEQ ID NO:2 with only 10 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:3 with only 1 additional amino acid at one terminal thereof and no additional amino acid at the other terminal thereof. In an embodiment, the isolated mutant PD-1 polypeptide consists of SEQ ID NO:3 with only 1 additional amino acid at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:3 with only 2 additional amino acids at one terminal thereof and no additional amino acid at the other terminal thereof. In an embodiment, the isolated mutant PD-1 polypeptide consists of SEQ ID NO:3 with only 2 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:3 with only 3 additional amino acids at one terminal thereof and no additional amino acid at the other terminal thereof. In an embodiment, the isolated mutant PD-1 polypeptide consists of SEQ ID NO:3 with only 3 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:3 with only 4 additional amino acids at one terminal thereof and no additional amino acid at the other terminal thereof. In an embodiment, the isolated mutant PD-1 polypeptide consists of SEQ ID NO:3 with only 4 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:3 with only 5 additional amino acids at one terminal thereof and no additional amino acid at the other terminal thereof. In an embodiment, the isolated mutant PD-1 polypeptide consists of SEQ ID NO:3 with only 5 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:3 with only 6 additional amino acids at one terminal thereof and no additional amino acid at the other terminal thereof. In an embodiment, the isolated mutant PD-1 polypeptide consists of SEQ ID NO:3 with only 6 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:3 with only 7 additional amino acids at one terminal thereof and no additional amino acid at the other terminal thereof. In an embodiment, the isolated mutant PD-1 polypeptide consists of SEQ ID NO:3 with only 7 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:3 with only 8 additional amino acids at one terminal thereof and no additional amino acid at the other terminal thereof. In an embodiment, the isolated mutant PD-1 polypeptide consists of SEQ ID NO:3 with only 8 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:3 with only 9 additional amino acids at one terminal thereof and no additional amino acid at the other terminal thereof. In an embodiment, the isolated mutant PD-1 polypeptide consists of SEQ ID NO:3 with only 9 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

In an embodiment, the isolated mutant PD-1 polypeptide consists of SEQ ID NO:3 with only 10 additional amino acids at one terminal thereof and no additional amino acid at the other terminal thereof. In an embodiment, the isolated mutant PD-1 polypeptide consists of SEQ ID NO:3 with only 10 additional amino acids at one terminal thereof and 1, 2, 3, 4, 5, 6, 7, 8, 9 or 10 additional amino acids at the other terminal thereof. In an embodiment, the one terminal thereof is the N-terminal. In an embodiment, the one terminal thereof is the C-terminal.

A fusion polypeptide is provided comprising a mutant PD-1 polypeptide comprising (i) SEQ ID NO:2, or (ii) SEQ ID NO:3 or (ii) having a sequence 95% or greater identical to SEQ ID NO:2 or SEQ ID NO:3, with the proviso that the mutant PD-1 polypeptide does not comprise SEQ ID NO:1, fused to a second polypeptide that does not naturally occur contiguous with (i), (ii), or (iii).

A fusion polypeptide is provided comprising a mutant PD-1 polypeptide comprising (i) SEQ ID NO:2, or (ii) SEQ ID NO:3, or (ii) having a sequence 95% or greater identical to SEQ ID NO:2 or SEQ ID NO:3, with the proviso that the mutant PD-1 polypeptide does not comprise SEQ ID NO:1, fused to an immunoglobulin domain polypeptide.

In an embodiment, the mutant PD-1 polypeptide is fused (bonded) to the immunoglobulin domain polypeptide by a peptide bond between a terminal amino acid of the mutant PD-1 polypeptide and a terminal amino acid of the immunoglobulin domain polypeptide. In an embodiment, the mutant polypeptide is fused to the immunoglobulin domain polypeptide by a linker molecule. In an embodiment, the linker molecule is a peptide. In an embodiment, the peptide linker permits flexibility. In an embodiment, the linker is rigid. In an embodiment the linker is cleavable. Non-limiting examples of flexible linkers within the scope of the invention are Gn, and GGGGS(SEQ ID NO: 38), and (GGGGS)n where n=2, 3, 4 or 5. Non-limiting examples of rigid linkers within the scope of the invention are (EAAAK)n (SEQ ID NO. 39), (XP)n where X=any amino acid. Non-limiting examples of cleavable linkers within the scope of the invention include disulfide links and protease cleavable linkers. In a preferred embodiment, the linker is a peptide linker.

In an embodiment, the immunoglobulin domain polypeptide comprises an immunoglobulin IgG1 Fc domain. In an embodiment, the immunoglobulin IgG1 Fc domain is human. In an embodiment, the immunoglobulin IgG1 Fc domain has the sequence of a human immunoglobulin IgG1 Fc domain. In an embodiment, the immunoglobulin IgG1 Fc domain is recombinant. In an embodiment, the immunoglobulin IgG1 Fc domain is not produced by a human body. Human igG1 Fc domain sequences and encoding nucleic acids are widely available in the art. For example, expressed from a DNA sequence encoding the human IgG1-Fc region (AAC82527.1). For example, recombinant human immunoglobulin IgG1 Fc domain expressed from a DNA sequence encoding the human IgG1-Fc region (AAC82527.1) containing residues 99 to 330, including a 103 Cys/Ser mutation (ThermoFisher Scientific®, Waltham, Mass., USA).

In an embodiment of the mutant polypeptide, the polypeptide is in monovalent form. In an embodiment of the fusion polypeptide, the fusion polypeptide is in monovalent form.

A homo-oligomer comprising a mutant polypeptide as described herein is also provided.

A homo-oligomer comprising a fusion polypeptide as described herein is also provided.

In an embodiment, the homo-oligomer comprises two mutant polypeptides of the same type as described herein. In an embodiment, the homo-oligomer comprises two mutant polypeptides of different types, each as described herein. In an embodiment, the homo-oligomer comprises two fusion polypeptides of the same type as described herein. In an embodiment, the homo-oligomer comprises two fusion polypeptides of different types, each as described herein.

Also provided is a composition comprising the mutant polypeptide as described herein.

Also provided is a composition comprising the fusion polypeptide as described herein.

Also provided is a composition comprising the homo-oligomer as described herein.

In an embodiment of the compositions, the composition comprises a pharmaceutically acceptable carrier.

Also provided is a method for stimulating T cell activation, treating a tumor, or treating an infection in a subject comprising administering to the subject the mutant polypeptide described herein or the mutant polypeptide-containing composition described herein, in an amount sufficient to stimulate T cell activation, treat a tumor, or treat an infection, respectively, in a subject. In an embodiment, the mutant polypeptide is administered in monovalent form. In an embodiment, the mutant polypeptide is administered as a homo-oligomer. In an embodiment, the method is for treating a tumor. In an embodiment, the method is for treating an infection. In an embodiment, the method is for stimulating T cell activation.

Also provided is a method for stimulating T cell activation, treating a tumor, or treating an infection in a subject comprising administering to the subject the fusion polypeptide described herein or the fusion polypeptide-containing composition described herein, in an amount sufficient to stimulate T cell activation, treat a tumor, or treat an infection, respectively, in a subject. In an embodiment, the fusion polypeptide is administered in monovalent form. In an embodiment, the fusion polypeptide is administered as a homo-oligomer. In an embodiment, the fusion polypeptide is a mutant polypeptide fused to an immunoglobulin domain polypeptide. In an embodiment, the mutant PD-1 polypeptide is fused to the immunoglobulin domain polypeptide by a peptide bond between a terminal amino acid of the mutant PD-1 polypeptide and a terminal amino acid of the immunoglobulin domain polypeptide. In an embodiment, the immunoglobulin domain polypeptide comprises an immunoglobulin IgG1 Fc domain. In an embodiment, the immunoglobulin IgG1 Fc domain is human.

In an embodiment of the methods, the T cell activation comprises cytokine secretion.

In an embodiment of the methods, the method is for treating a tumor.

In an embodiment of the methods, the polypeptide, or the fusion peptide, respectively, comprises SEQ ID NO:3. In an embodiment of the methods, the method is for treating a tumor and the tumor is a PD-L2-expressing tumor.

In an embodiment of the methods, the polypeptide, or the fusion peptide, respectively, comprises SEQ ID NO:2. In an embodiment of the methods, the method is for treating a tumor and the tumor is a PD-L1-expressing tumor or is a PD-L1-expressing and PD-L2-expressing tumor.

In an embodiment of the methods, the method is for treating an infection.

Also provided is an isolated nucleic acid encoding a mutant PD-1 polypeptide as described herein. Also provided is an isolated nucleic acid encoding a fusion polypeptide comprising the mutant PD-1 polypeptide as described herein. In an embodiment, the nucleic acid has been labeled with a synthetic marker. In an embodiment, the nucleic acid is a recombinant nucleic acid. In an embodiment, the nucleic acid comprises cDNA.

An isolated cell is provided containing a vector comprising an isolated nucleic acid as described herein. In an embodiment, the cell is a mammalian cell. In an embodiment, the cell is not in a human. In an embodiment, the cell is derived from a mammalian cell.

This invention provides an isolated polypeptide having the following sequence:

(SEQ ID NO: 2)
WNPPTFSPALLVVTEGDNATFTCSFSNTSEX$_1$FX$_2$LNWYRX$_3$SX$_4$SNQTD

KLAAFPEDRSQPGQDCRFRVTQLPNGRDFHMSVVRARRNDSGTYX$_5$CAAI

X$_6$X$_7$X$_8$PX$_9$X$_{10}$QX$_{11}$KESLRAELRVTERRAEVPTAHPSPSP

Wherein:
X1=S or A
X2=V or I
X3=L or M
X4=P or A
X5=L or I
X6=A or S
X7=L or I
X8=A or S
X9=R or K
X10=A or S
X11=I or V.

In an embodiment, this polypeptide binds to PD-L1 and to PD-L2. In an embodiment, the polypeptide having SEQ ID NO:2 does not comprise SEQ ID NO:1. In an embodiment, the polypeptide having SEQ ID NO:2 does not comprise SEQ ID NO:3.

This invention provides an isolated polypeptide having the following sequence:

(SEQ ID NO: 3)
WNPPTFSPALLVVTEGDNATFTCSFSNTSEX$_{12}$FX$_{13}$LNWYRX$_{14}$X$_{15}$X$_{16}$

X$_{17}$X$_{18}$QTDKLAAFPEDRSQX$_{19}$GQDCRFRVTQLPNGRDFHMSVVRARRN

DSGTYX$_{20}$CAAX$_{21}$X$_{22}$X$_{23}$X$_{24}$X$_{25}$X$_{26}$X$_{27}$QX$_{28}$KESLRAELRVTERR

AEVPTAHPSPSP

Wherein:
X12=S or A
X13=V or I
X14=L or M
X15=S or A
X16=P or A
X17=S or A
X18=N or D
X19=P or S
X20=L or I
X21=I or V
X22=A or S
X23=L or I
X24=A or S
X25=P or A
X26=R or K
X27=A or S
X28=I or V.

In an embodiment, this polypeptide binds to PD-L2. In an embodiment, this polypeptide binds to PD-L2 but not to PD-L1. In an embodiment, the polypeptide having SEQ ID NO:3 does not comprise SEQ ID NO:1. In an embodiment, the polypeptide having SEQ ID NO:3 does not comprise SEQ ID NO:2.

In an embodiment, the polypeptide of the invention as described herein is not naturally occurring.

In an embodiment, the polypeptide is in monovalent form. In an embodiment, the mutant polypeptide is soluble. In an embodiment, the mutant polypeptide does not comprise a transmembrane domain. In an embodiment, the mutant polypeptide does not comprise a intracellular domain. In an embodiment, the mutant polypeptide further comprises a sequence having the same sequence as a PD-1 transmembrane domain. In an embodiment, the mutant polypeptide does not further comprise a sequence having the same sequence as a PD-1 transmembrane domain. In an embodiment, the mutant polypeptide further comprises a sequence having the same sequence as a PD-1 intracellular domain. In an embodiment, the mutant polypeptide does not further comprise a sequence having the same sequence as a PD-1 intracellular domain.

In an embodiment, the mutant PD-1 polypeptide comprises consecutive amino acid residues (i) having the sequence set forth in SEQ ID NO:2, or (ii) having a sequence 95% or greater identical to SEQ ID NO:2, but wherein in (ii) the polypeptide has the following residues at the same positions as set forth in SEQ ID NO:2:
X1=S or A
X2=V or I
X3=L or M
X4=P or A
X5=L or I
X6=A or S
X7=L or I
X8=A or S
X9=R or K
X10=A or S
X11=I or V.

In an embodiment, the mutant PD-1 polypeptide comprises consecutive amino acid residues having a sequence 96% or greater identical to SEQ ID NO:2. In an embodiment, the mutant PD-1 polypeptide comprises consecutive amino acid residues having a sequence 97% or greater identical to SEQ ID NO:2. In an embodiment, the mutant PD-1 polypeptide comprises consecutive amino acid residues having a sequence 98% or greater identical to SEQ ID NO:2. In an embodiment, the mutant PD-1 polypeptide comprises consecutive amino acid residues having a sequence 99% or greater identical to SEQ ID NO:2. In an embodiment the mutant PD-1 polypeptide does not comprise SEQ ID NO:1.

In an embodiment, the mutant PD-1 polypeptide comprises consecutive amino acid residues (i) having the sequence set forth in SEQ ID NO:3, or (ii) having a sequence 95% or greater identical to SEQ ID NO:3, but wherein in (ii) the polypeptide has the following residues at the same positions as set forth in SEQ ID NO:3:
X12=S or A
X13=V or I
X14=L or M
X15=S or A
X16=P or A
X17=S or A
X18=N or D
X19=P or S
X20=L or I
X21=I or V
X22=A or S
X23=L or I
X24=A or S
X25=P or A
X26=R or K
X27=A or S
X28=I or V.

In an embodiment, the mutant PD-1 polypeptide comprises consecutive amino acid residues having a sequence 96% or greater identical to SEQ ID NO:3. In an embodiment, the mutant PD-1 polypeptide comprises consecutive amino acid residues having a sequence 97% or greater identical to SEQ ID NO:3. In an embodiment, the mutant PD-1 polypeptide comprises consecutive amino acid residues having a sequence 98% or greater identical to SEQ ID NO:3. In an embodiment, the mutant PD-1 polypeptide comprises consecutive amino acid residues having a sequence 99% or greater identical to SEQ ID NO:3. In an embodiment the mutant PD-1 polypeptide does not comprise SEQ ID NO:1.

Substitution variants of the mutant PD-1, as provided by the invention, have at least one amino acid residue in the polypeptide removed and a different residue inserted in its place (except for the conserved residues X1 through X11 of SEQ ID NO:2; and except for the conserved residues X12 through X28 of SEQ ID NO:3). In an embodiment, the substitution is a conservative substitution. Conservative substitutions are shown in Table 1 under the heading of "conservative substitutions." In an embodiment, the substitution is an exemplary substitution as listed in Table 1. In an embodiment, the PD-1 mutant contains one of 1, 2, 3, 4 or 5 substitutions relative to SEQ ID NO:2 or SEQ ID NO:3:

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

This invention also provides a fusion polypeptide comprising the isolated mutant PD-1 polypeptide described herein, fused to an immunoglobulin domain polypeptide. In an embodiment, the mutant PD-1 polypeptide is fused to the immunoglobulin domain polypeptide by a peptide bond between a terminal amino acid of the mutant PD-1 polypeptide and a terminal amino acid of the immunoglobulin domain polypeptide. In an embodiment, the mutant PD-1 polypeptide is fused to the immunoglobulin domain polypeptide by a linker peptide between a terminal amino acid of the mutant PD-1 polypeptide and a terminal amino acid of the immunoglobulin domain polypeptide. In an embodiment, the immunoglobulin domain polypeptide comprises an immunoglobulin IgG Fc domain. In an embodiment, the immunoglobulin domain polypeptide comprises an immunoglobulin IgM Fc domain. In an embodiment, the immunoglobulin domain polypeptide comprises an immunoglobulin IgG1 Fc domain. In an embodiment, the immunoglobulin IgG or IgM Fc domain is human. In an embodiment, the immunoglobulin IgG1 Fc domain is human. In an embodiment, the fusion polypeptide is in monovalent form. In an embodiment, the fusion polypeptide comprises SEQ ID NO:2 as disclosed herein.

This invention also provides a homo-oligomer comprising the isolated mutant PD-1 polypeptide, or comprising the fusion polypeptide. In a preferred embodiment, the homo-oligomer comprises two of the isolated polypeptides, or two of the fusion polypeptides.

This invention also provides a composition comprising the isolated polypeptide in monovalent form or oligomeric form. This invention also provides a composition comprising the fusion polypeptide in monovalent form or oligomeric form. In an embodiment, the compositions comprise a pharmaceutically acceptable carrier. In an embodiment, the pharmaceutically acceptable carrier comprises a single type of molecule. In an embodiment, the pharmaceutically acceptable carrier comprises a mixture of molecules.

Using Fc-fusion polypeptides are widely known in the art. See, for example, Czajkowsky D M et al., EMBO Mol Med. 2012 October; 4(10): 1015-1028, hereby incorporated by reference.

Also provided is a method of stimulating T cell activation in a subject comprising administering to the subject the isolated mutant PD-1 polypeptide described herein, or the composition or homo-oligomer comprising the isolated mutant PD-1 polypeptide described herein, in an amount sufficient to stimulate T cell activation in a subject. In an embodiment, the subject has a tumor. In an embodiment, the subject has an infection.

Also provided is a method of treating a tumor in a subject comprising administering to the subject the isolated fusion polypeptide comprising the mutant PD-1 described herein, or the composition or homo-oligomer comprising the isolated fusion polypeptide comprising the mutant PD-1 described herein, in an amount sufficient to treat a tumor in a subject.

In an embodiment, the tumor is on of a breast, lung, colon, ovarian, melanoma, bladder, liver, salivary, stomach, gliomas, thyroid, thymus, epithelial, head, or neck tumor. Each of these tumors is also provided herein as an independent, individual embodiment. In an embodiment, the tumor is a hematological malignancy. In an embodiment, the tumor is a lymphoma. In an embodiment, the tumor is a myeloma. In an embodiment, the tumor is a multiple myeloma. In an embodiment, the tumor is a PD-L2 expressing tumor. In an embodiment, the PD-L2 expressing tumor is a pancreatic tumor. In an embodiment, the PD-L2 expressing tumor is a esophageal tumor.

Also provided is a method of treating an infection in a subject comprising administering to the subject the isolated fusion polypeptide described herein, or the composition or homo-oligomer comprising the isolated fusion polypeptide described herein, in an amount sufficient to treat an infection in a subject.

In an embodiment, the infection is a viral infection. In a further embodiment, the virus is a HIV, HCV, HBV or HTLV. In an embodiment, the infection is a bacterial, fungal, protozoal or parasitic infection. In embodiments, the infection is caused by *Helicobacter pylori*, the fungus *Histoplasma capsulatum*, the parasite *Taenia crassiceps* or *Schistosoma mansoni*, or the protozoa *Leishmania mexicana*. Each of these infections is also provided herein as an independent, individual embodiment.

In an embodiment, the composition is a pharmaceutical composition. In an embodiment, the pharmaceutical composition comprises a pharmaceutically acceptable carrier. As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

Also provided is an isolated nucleic acid encoding an isolated mutant PD-1 polypeptide described herein. Also provided is an isolated nucleic acid encoding a fusion polypeptide comprising the mutant PD-1 described herein. In an embodiment the encoded fusion protein comprises a human Fc sequence. In an embodiment, the nucleic acid is a recombinant nucleic acid. In an embodiment, the nucleic acid is an RNA. In an embodiment, the nucleic acid is a DNA. In an embodiment, the nucleic acid comprises cDNA.

An isolated cell containing a vector comprising a nucleic acid encoding an isolated mutant PD-1 polypeptide described herein is also provided. In an embodiment, the cell is used for production of the mutant PD-1 polypeptide.

As described herein, a mutant PD-1 polypeptide is not a naturally occurring mutant PD-1 polypeptide.

Also provided is an isolated mutant PD-1 polypeptide, as described hereinabove, or a fusion polypeptide comprising the polypeptide, as described hereinabove, fused to an immunoglobulin domain polypeptide, for treating an infection in a subject, or for treating a tumor in a subject, or for stimulating T-cell activation in a subject. In an embodiment, the mutant PD-1 polypeptide is for treating an infection in a subject. Exemplary infections are described hereinabove. In an embodiment, the mutant PD-1 polypeptide is for treating a tumor in a subject. Exemplary tumors are described hereinabove. In an embodiment, the mutant PD-1 polypeptide is for stimulating T-cell activation in a subject.

In a preferred embodiment of the methods, the subject is a human.

Also provided is a composition comprising a dendritic cell, loaded with any of the isolated mutant polypeptides or fusion proteins described herein. In an embodiment, the dendritic cell is mammalian. In an embodiment, it is derived from a human. In an embodiment, it is not derived from a human.

In an embodiment, the isolated mutant PD-1 polypeptide as described herein is capable of preferentially binding to a human PD-L2 over a PD-L1. In an embodiment, the isolated mutant PD-1 polypeptide as described herein specifically binds to a human PD-L2, with binding to PD-L1 undetectable. In an embodiment, the isolated mutant PD-1 polypeptide as described herein is capable of preferentially binding to a human PD-L1 over a PD-L2.

In an embodiment of the inventions set forth herein comprising SEQ ID NO:2, the sequence is any one of SEQ ID NOS:4-16. In an embodiment, the sequence is SEQ ID NO:4. In an embodiment, the sequence is SEQ ID NO:5. In an embodiment, the sequence is SEQ ID NO:6. In an embodiment, the sequence is SEQ ID NO:7. In an embodiment, the sequence is SEQ ID NO:8. In an embodiment, the sequence is SEQ ID NO:9. In an embodiment, the sequence is SEQ ID NO:10. In an embodiment, the sequence is SEQ ID NO:11. In an embodiment, the sequence is SEQ ID NO:12. In an embodiment, the sequence is SEQ ID NO:13. In an embodiment, the sequence is SEQ ID NO:14. In an embodiment, the sequence is SEQ ID NO:15. In an embodiment, the sequence is SEQ ID NO:16.

In an embodiment of the inventions set forth herein comprising SEQ ID NO:3, the sequence is any one of SEQ ID NOS:17-37. In an embodiment, the sequence is SEQ ID NO:17. In an embodiment, the sequence is SEQ ID NO:18. In an embodiment, the sequence is SEQ ID NO:19. In an embodiment, the sequence is SEQ ID NO:20. In an embodiment, the sequence is SEQ ID NO:21. In an embodiment, the sequence is SEQ ID NO:22. In an embodiment, the sequence is SEQ ID NO:23. In an embodiment, the sequence is SEQ ID NO:24. In an embodiment, the sequence is SEQ ID NO:25. In an embodiment, the sequence is SEQ ID NO:26. In an embodiment, the sequence is SEQ ID NO:27. In an embodiment, the sequence is SEQ ID NO:28. In an embodiment, the sequence is SEQ ID NO:29. In an embodiment, the sequence is SEQ ID NO:30. In an embodiment, the sequence is SEQ ID NO:31. In an embodiment, the sequence is SEQ ID NO:32. In an embodiment, the sequence is SEQ ID NO:33. In an embodiment, the sequence is SEQ ID NO:34. In an embodiment, the sequence is SEQ ID NO:35. In an embodiment, the sequence is SEQ ID NO:36. In an embodiment, the sequence is SEQ ID NO:37.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

In recent years, the targeting of T cell costimulatory pathways has been demonstrated to represent powerful and effective strategies for immunotherapy. The best characterized costimulatory pathways include those associated with members of the CD28:B7 family, such as CD28 and ICOS as positive co-receptors, and CTLA4 and PD-1 as co-inhibitors. Herein, structure-guided approaches have been used to develop a novel protein reagent by engineering the human PD-1 sequence.

Results

Phage display was used to engineer the wild type human PD-1 IgV domain with two objectives in mind: (i) to identify engineered PD-1 IgV variants (ePD-1s) that bind both PD-L1 and PD-L2 with high affinity; (ii) to identify ePD-1s that preferentially bind to PD-L2 with enhanced specificity. Previously, yeast display have been used to engineer high affinity PD-L1-specific PD-1 variants for therapeutic and diagnostic/imaging application: Proc Natl Acad Sci USA. 2015 Nov. 24; 112(47):E6506-14. Herein it was speculated that the natural "bispecific" recognition tendencies already inherent in PD-1 for binding to both PD-L1 and PD-L2 might be enhanced simultaneously to create higher affinity variants that are still bispecific for both ligands. Furthermore, although PD-L1 is more widely expressed than PD-L2, there are several cancers in which PD-L2 is dominantly expressed thus high-affinity PD-L2-specific (ePD-1)$_2$-Fc molecules (fusion polypeptides) could be used as specific therapeutics or diagnostics in those cases.

The human PD-1 IgV domain was expressed on M13 bacteriophage as a fusion to the pIII coat protein. Using the murine PD-1/PD-L1 and PD-1/PD-L2 crystal structures, and previous mutagenesis results as our guide, a homolog scanning library in which selected residues (elaborated in FIG. 1) were allowed to vary among their WT residue identify or homologous residues. The variations may allow "optimization" of minor contact or supporting conformations to enhance or change specificity. This library was subjected to two different selection schemes: (i) "Bi" a toggle selection between PD-L1 and PD-L2; (ii) "L2" a selection only against PD-L2. A number of hits were been characterized by phage ELISA and were sequenced. A number of cross-reactive clones that bind both PD-L1 and PD-L2 at low phage titer were been identified (FIG. 2, 3). The affinity of these relative to WT PD-1 is assessed. Furthermore, several PD-L2-specific ePD-1s were identified, in which there is no binding to PD-L1 observed (FIG. 4, 5). The ePD-1s were expressed and purified (gel data not shown).

Equilibrium dissociation constants ($K_d$s) can be determined by non-linear fitting of SPR data using, for example, immobilized PD-1 Ligands (e.g. PD-L1 and/or PD-L2) and soluble wild-type or mutant PD-1. $K_d$ values can be expressed in, for example, μM concentration, followed by the standard errors of the fittings. Human monocyte-derived dendritic cells expressing PD-L1 and PD-L2 are one exemplary target. $K_d$ values of 10 down to 1 pM are of most use. Preferred $K_d$ values are 1 μM or below.

Dimeric soluble Fc chimera of the mutant PD-1 polypeptides can be further engineered, for example, by fusing a mutant PD-1 polypeptide to the Fc part of human IgG1.

Discussion

Blocking the PD-1/PD-L pathways using the mutant PD-1 polypeptides or mutant PD-1 Ig fusion proteins disclosed herein would result in an enhanced immune response, similar to that of the CTLA-4 blockade caused by Yervoy; however, due to differences in the roles of the CTLA-4/B7 and the PD-1/PD-L pathways, less severe side effects would be seen with PD-1 blockade. Due to the expression patterns of PD-1 and its ligands on both peripheral and immune cells (unlike CTLA-4 and its ligands which are expressed on immune cells only), the paradigm is that PD-1/PD-L pathway predominantly regulates peripheral immune responses at the tissue level (with a lesser role in central immunity than CTLA-4), consistent with its major role in peripheral tolerance. Yervoy (anti-CTLA-4) targets predominantly interactions between T cells and APCs, and is thus expected to cause systemic immune stimulation accompanied by adverse effects. In contrast, due to the large number of studies reporting upregulation of PD-Ls on infected cells and tumor cells, the high-affinity mutant PD-1 Ig fusion protein would preferentially bind to these target cells and act primarily on T cells (effectors) that are specifically recruited to these sites, as opposed to the systemic immune activation elicited by an antibody that binds to and activates all T cells.

An additional advantage is conferred by the mutant PD-L2 specific polypeptides disclosed herein. These can be used, alone or, for example, as fusion protein constructs, to treat PD-L2 expressing tumors with less off-target effects than agents that bind both PD-L1 and PD-L2.

Specific therapeutic targets for the agents disclosed herein are numerous. Both chronic infections and malignant tumors affect increasing numbers of patients not just in the US but worldwide. Chronic infections such as HIV, and HCV affect 33 million and 170 million people worldwide, respectively, as well as HBV infection which affects about 2 billion people worldwide (the most common infectious disease today). Acute infections in which the PD-1 pathway is involved, such as histoplasmosis, are also prevalent (50 million people affected in North America), as are rabies and RSV infections. Malignancies constitute another major area that could be targeted for treatment using the agents of invention. The incidence of tumors continues to increase worldwide; currently about 12.7 million new cases are reported each year. The incidence of cancer cases is highest for Australia/New Zealand, North America and Europe, where treatment is also more available or sought-after. Since several tumor cell types upregulate ligands of inhibitory receptors, such as PD-L1 and PD-L2, to promote immune evasion, administration of the agents disclosed herein is expected to be beneficial in such states. Natural immunological clearance of tumors is rare, due to the immunosuppressive environment generated by the developing tumor. As part of this immunosuppressive mechanism, many tumors upregulate ligands of inhibitory receptors such as PD-L1 and PD-L2. PD-L1 has been shown to be upregulated on a variety of solid tumors, such as breast, lung, colon, ovarian, melanoma, bladder, liver, salivary, stomach, gliomas, thyroid, thymic, epithelial, head, and neck (Keir M E et al, *Annu Rev Immunol* 2008). Both PD-Ligands have been shown to be upregulated in hematologic malignancies such as lymphomas and multiple myeloma. In addition, PD-1 is upregulated on tumor infiltrating lymphocytes, which is also expected to contribute to tumor immunosuppression. In addition, HA PD-1 Ig can be beneficial to treat tumors that do not express PD-Ls (although less efficient, compared to PD-L-expressing tumors), by causing immune activation at the level of initial antigen presentation to T cells (an analogous mechanism to that of CTLA4 blockade).

Since the mutant PD-1 ligands can bind the PD-Ligands with high affinity, they will prevent inhibitory signals into tumor infiltrating T cells through the endogenous PD-1 receptor. Removal of these inhibitory signals has dramatic effects on anti-tumor immune responses (e.g. as observed with Yervoy, a CTLA-4-specific monoclonal antibody, approved by FDA for the treatment of metastatic melanoma), the fusion polypeptide can be used in the malignancies listed above to activate the tumor-specific T cell response and induce tumor regression. In addition, the PD-L2-specific mutant ligands can be used to treat PD-L2-expressing disease states. For example, esophageal and pancreatic cancers have both been found to express PD-L2.

REFERENCES

Hodi F S et al., *N Engl J Med* (2010), 363:711-723.
Keir M E et al, *Annu Rev Immunol* (2008), 26:677-704
Czajkowsky D M et al., *EMBO Mol Med.* 2012 October; 4(10): 1015-1028

What is claimed is:

1. An isolated mutant programmed cell death 1 (PD-1) polypeptide comprising (i) SEQ ID NO: 2, (ii) SEQ ID NO: 3, or (iii) an amino acid sequence having at least 99% identity to SEQ ID NO: 2 or SEQ ID NO: 3 with the proviso that the mutant PD-1 polypeptide does not comprise SEQ ID NO: 1;
   wherein the polypeptide does not comprise (i) SEQ ID NO:_2, wherein position 41 is an A and position 91 is an I, (ii) SEQ ID NO:_3, wherein position 41 is an A and position 91 is an I, or (iii) an amino acid sequence having at least 99% identity to SEQ ID NO:_2 or SEQ ID NO:_3, wherein position 41 is an A and position 91 is an I.

2. The polypeptide of claim 1, comprising SEQ ID NO: 2.

3. The polypeptide of claim 1, comprising SEQ ID NO: 3.

4. A fusion polypeptide comprising the polypeptide of claim 1 fused to an immunoglobulin domain polypeptide.

5. The fusion polypeptide of claim 4, wherein the mutant PD-1 polypeptide is fused to the immunoglobulin domain polypeptide by a peptide bond between a terminal amino acid of the mutant PD-1 polypeptide and a terminal amino acid of the immunoglobulin domain polypeptide.

6. The fusion polypeptide of claim 4, wherein the immunoglobulin domain polypeptide comprises an immunoglobulin IgG1 Fc domain.

7. The fusion polypeptide of claim 6, wherein the immunoglobulin IgG1 Fc domain is human.

8. The polypeptide of claim 1 in monovalent form.

9. A homo-oligomer comprising the polypeptide of claim 1.

10. The homo-oligomer of claim 9, comprising two polypeptides.

11. A composition comprising the polypeptide of claim 1.

12. A composition comprising the fusion polypeptide of claim 4.

13. A composition comprising the homo-oligomer of claim 9.

14. The composition of claim 11, comprising a pharmaceutically acceptable carrier.

15. An isolated nucleic acid encoding the isolated mutant PD-1 polypeptide of claim 1.

16. An isolated nucleic acid encoding the fusion polypeptide of claim 4.

17. The nucleic acid of claim 15, which is a recombinant nucleic acid.

18. The nucleic acid of claim 15, which comprises cDNA.

19. An isolated cell containing a vector comprising a nucleic acid of claim 15.

* * * * *